United States Patent
Ulrichts et al.

(10) Patent No.: US 11,505,585 B2
(45) Date of Patent: Nov. 22, 2022

(54) FCRN ANTAGONISTS AND METHODS OF USE

(71) Applicants: argenx BV, Zwijnaarde (BE); THE BOARD OF REGENTS OF THE UNIVERSITY OF TEXAS SYSTEM, Austin, TX (US)

(72) Inventors: Peter Ulrichts, Destelbergeb (BE); Christophe Blanchetot, Destellbergen (BE); Torsten Dreier, Sint Martens Latem (BE); Johannes de Haard, NA Oudelande (NL); E. Sally Ward Ober, Dallas, TX (US); Nicolas G. H. Ongenae, Ghent (BE)

(73) Assignees: argenx BV, Ghent (BE); The Board of Regents of the University of Texas System, Austin, TX (US)

( * ) Notice: Subject to any disclaimer, the term of this patent is extended or adjusted under 35 U.S.C. 154(b) by 412 days.

(21) Appl. No.: 15/821,104

(22) Filed: Nov. 22, 2017

(65) Prior Publication Data

US 2018/0179258 A1    Jun. 28, 2018

Related U.S. Application Data

(62) Division of application No. 14/580,771, filed on Dec. 23, 2014, now Pat. No. 10,316,073.

(60) Provisional application No. 61/920,547, filed on Dec. 24, 2013.

(51) Int. Cl.
| | | |
|---|---|---|
| A61K 39/395 | (2006.01) | |
| A61K 39/40 | (2006.01) | |
| C07K 14/47 | (2006.01) | |
| A61K 45/06 | (2006.01) | |
| A61K 38/17 | (2006.01) | |
| C07K 1/00 | (2006.01) | |
| A61K 38/00 | (2006.01) | |

(52) U.S. Cl.
CPC ...... *C07K 14/4703* (2013.01); *A61K 38/1709* (2013.01); *A61K 45/06* (2013.01); *A61K 38/00* (2013.01); *C07K 2317/41* (2013.01); *C07K 2317/52* (2013.01); *C07K 2317/524* (2013.01); *C07K 2317/526* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,326,856 A | 7/1994 | Coughlin et al. |
| 5,624,821 A | 4/1997 | Winter et al. |
| 5,648,260 A | 7/1997 | Winter et al. |
| 5,677,425 A | 10/1997 | Bodmer et al. |
| 5,869,046 A | 2/1999 | Presta et al. |
| 5,885,573 A | 3/1999 | Bluestone et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,528,624 B1 | 3/2003 | Idusogie et al. |
| 6,737,056 B1 | 5/2004 | Presta |
| 6,795,661 B2 | 9/2004 | Kanesawa et al. |
| 6,821,505 B2 | 11/2004 | Ward |
| 6,992,234 B2 | 1/2006 | Roopenian et al. |
| 7,083,784 B2 | 8/2006 | Dall'acqua et al. |
| 7,670,600 B2 | 3/2010 | Dall'acqua et al. |
| 7,683,784 B2 | 3/2010 | Nagai et al. |
| 7,704,497 B2 | 4/2010 | Dall'Acqua et al. |
| 8,012,476 B2 | 9/2011 | Dall'Acqua et al. |
| 8,021,856 B2 | 9/2011 | Umaña et al. |
| 8,067,232 B2 | 11/2011 | Kanda |
| 8,101,186 B2 | 1/2012 | Mezo et al. |
| 8,163,881 B2 | 4/2012 | Ober |
| 8,195,661 B2 | 6/2012 | Asawaree |
| 8,216,805 B2 | 7/2012 | Carter et al. |
| 8,273,351 B2 | 9/2012 | Tenhoor et al. |
| 8,323,962 B2 | 12/2012 | Dall'Acqua et al. |
| 8,475,792 B2 | 7/2013 | Dall'Acqua et al. |

(Continued)

FOREIGN PATENT DOCUMENTS

| | | |
|---|---|---|
| EP | 0227110 A2 | 7/1987 |
| EP | 0 904 107 B1 | 3/1999 |

(Continued)

OTHER PUBLICATIONS

Evoli et al. Autoimmunity Review, 2013, 12: 931-935. (Year: 2013).*
Li et al., Cleveland Clinic Journal of Medicine 80(11): 711-721. (Year: 2013).*
Silvestri et al. Journal of Clinical Neuromuscular Disease, 2014, 15(4): 167-178. (Year: 2014).*

(Continued)

*Primary Examiner* — Chun W Dahle

(74) *Attorney, Agent, or Firm* — Dechert LLP; Andrew T. Wilkins; Sharla F. Flohr

(57) ABSTRACT

Provided are novel FcRn antagonist compositions comprising a variant Fc region that binds specifically to FcRn with increased affinity and reduced pH dependence relative to the native Fc region. Also provided are FcRn antagonists with enhanced CD16 binding affinity. Also provided are methods of treating antibody-mediated disorders (e.g. autoimmune diseases) using the these FcRn antagonist compositions, nucleic acids encoding the FcRn antagonist compositions, recombinant expression vectors and host cells for making the FcRn antagonist compositions, and pharmaceutical compositions comprising the FcRn antagonist compositions.

10 Claims, 10 Drawing Sheets

Specification includes a Sequence Listing.

(56) References Cited

U.S. PATENT DOCUMENTS

| | | | |
|---|---|---|---|
| 8,680,237 B2* | 3/2014 | Strome | C07K 16/065 530/350 |
| 8,795,661 B2 | 8/2014 | Dall'Acqua et al. | |
| 8,815,246 B2 | 8/2014 | Tenhoor et al. | |
| 8,834,871 B2 | 9/2014 | Ober | |
| 9,260,520 B2 | 2/2016 | Tenhoor et al. | |
| 10,316,073 B2 | 6/2019 | Ulrichs | |
| 2004/0002587 A1 | 1/2004 | Watkins et al. | |
| 2004/0010124 A1 | 1/2004 | Johnson et al. | |
| 2004/0047862 A1 | 3/2004 | Lazarus et al. | |
| 2004/0265321 A1 | 12/2004 | Johnson et al. | |
| 2007/0041907 A1 | 2/2007 | Ober | |
| 2007/0092507 A1 | 4/2007 | Balthasar et al. | |
| 2009/0252729 A1 | 10/2009 | Farrington et al. | |
| 2011/0081345 A1 | 4/2011 | Moore | |
| 2011/0243966 A1 | 10/2011 | Farrington et al. | |
| 2012/0219551 A1 | 8/2012 | Johnson | |
| 2013/0142802 A1 | 6/2013 | Chang et al. | |
| 2014/0302028 A1 | 10/2014 | Zha et al. | |
| 2015/0218239 A1 | 8/2015 | Ulrichts et al. | |
| 2016/0264669 A1 | 9/2016 | Ulrichts et al. | |

FOREIGN PATENT DOCUMENTS

| | | |
|---|---|---|
| EP | 1 355 919 B1 | 11/2010 |
| EP | 1 896 503 B1 | 10/2014 |
| JP | 2013-507128 A | 3/2013 |
| WO | WO 1994/029351 A2 | 12/1994 |
| WO | 1996/022024 A1 | 7/1996 |
| WO | 1997/034631 A1 | 9/1997 |
| WO | 1999/004813 A1 | 2/1999 |
| WO | WO 1999/058572 A1 | 11/1999 |
| WO | WO 2000/042072 A2 | 7/2000 |
| WO | WO 2001/058957 A2 | 8/2001 |
| WO | 2002/043658 A2 | 6/2002 |
| WO | 2002/060919 A2 | 8/2002 |
| WO | WO 2004/016750 A2 | 2/2004 |
| WO | WO 2004/029207 A2 | 4/2004 |
| WO | WO 2004/035752 A2 | 4/2004 |
| WO | WO 2004/063343 A2 | 7/2004 |
| WO | WO 2004/063351 A2 | 7/2004 |
| WO | WO 2004/099249 A2 | 11/2004 |
| WO | WO 2005/040217 A2 | 5/2005 |
| WO | 2006/118772 A2 | 11/2006 |
| WO | WO 2006/118772 A2 | 11/2006 |
| WO | 2006/130834 A2 | 12/2006 |
| WO | 2007/098420 A2 | 8/2007 |
| WO | 2009/100105 A2 | 8/2009 |
| WO | 2009/131702 A2 | 10/2009 |
| WO | 2010/014909 A1 | 2/2010 |
| WO | 2010/106180 A2 | 9/2010 |
| WO | 2011/044368 A1 | 4/2011 |
| WO | WO 2013/000702 A1 | 1/2013 |
| WO | 2013/074598 A1 | 5/2013 |
| WO | WO 2013/063186 A2 | 5/2013 |
| WO | 2013100702 A1 | 7/2013 |
| WO | WO 2014/008391 A1 | 1/2014 |
| WO | 2014/019727 A1 | 2/2014 |
| WO | 2014/204280 A1 | 12/2014 |
| WO | 2015/081073 A2 | 6/2015 |
| WO | 2015/100299 A1 | 7/2015 |
| WO | WO 2015/100299 A1 | 7/2015 |
| WO | WO 2016/042083 A1 | 3/2016 |
| WO | 2016/123521 A2 | 8/2016 |
| WO | 2016/142782 A1 | 9/2016 |
| WO | 2016/183352 A1 | 11/2016 |
| WO | WO 2016/180765 A1 | 11/2016 |
| WO | WO 2016/180765 A1 | 11/2016 |
| WO | WO 2017/012959 A1 | 1/2017 |
| WO | 2017/121330 A1 | 7/2017 |
| WO | WO 2018/083122 A1 | 5/2018 |
| WO | WO 2019/110823 A1 | 6/2019 |
| WO | WO 2019/234713 A2 | 12/2019 |
| WO | WO 2020/236695 A1 | 11/2020 |

OTHER PUBLICATIONS

Joshi et al. Inflammation & Allergy—Drug Targets, 2014, 13: 249-261. (Year: 2014).*

Rosenwasser et al. Clinical Reviews in Allergy and Immunology, 2005, 29:61-72. (Year: 2005).*

Akilesh et al. (2004) "The MHC class I-like Fc receptor promotes humorally mediated autoimmune disease," J. Clin. Invest. 113(9): 1328-1333.

ARGEN-X "ARGX-113," http://www.argen-x.com. Accessible on the Internet at URL: http://www.argen-x.com/en-GB/content/argx-113/22. [Last Accessed Jul. 5, 2017].

ARGEN-X (Oct. 2013) "An Emerging Antibody Force: Company Presentation," Presentation Slides.

ARGEN-X (Oct. 2013) "ARGX-113: Development Opportunity in Autoimmunity," Presentation Slides.

Ballow (1991) "Mechanism of action of IVIG therapy and potential uses in autoimmune connective tissue diseases," Cancer 68:1430-1436.

Barth et al. (2011) "Comparison of IVIg and PLEX in patients with myasthenia gravis," Neurology. 76(23):2017-2023.

Blanchette et al. (1984) "Intensive plasma exchange therapy in ten patients with idiopathic thrombocytopenic purpura," Transfusion. 24(5):388-394.

Burns (2012) "Of Mice and Children: Lessons From a Kawasaki Mouse Model," Circulation. 125:1480-1481.

Burns et al. (2010) "History of outcome measures for myasthenia gravis," Muscle Nerve. 42(1):5-13.

Challa et al. (Jun. 19, 2013) "Autoantibody depletion ameliorates disease in murine experimental autoimmune ancephalomyelitis," MAbs. 5(5):655-659.

Cipriani et al. (2009) "MET as a target for treatment of chest tumor," Lung Cancer. 63(2):169-179.

Coetzee et al. (2000) "The Effect of Monoclonal Anti-human-platelet Antibodies on Platelet Kinetics in a Baboon Model: IgG Subclass Dependency," Thromb. Haemost. 83:148-156.

Crow et al. (2008) "The Mechanisms of Action of Intravenous Immunoglobulin and Polyclonal Anti-D Immunoglobulin in the Amelioration of Immune Thrombocytopenic Purpura: What Do We Really Know?" Transfusion Medicine Reviews. 22:103-116.

Crow et al. (2011) "The neonatal Fc receptor (FcRn) is not required for IVIg or anti-CD44 monoclonal antibody-mediated amelioration of murine immune thrombocytopenia," Blood. 118:6403-6406.

Darabi et al. (2006) "Current usage of intravenous immune globulin and the rationale behind it: the Massachusetts General Hospital data and a review of the literature," Transfusion. 46(5):741-753.

Debre et al. (1993) "Infusion of Fc gamma fragments for treatment of children with acute immune thrombocytopenic Durpura," Lancet. 342(8877):945-949.

Deng et al. (2007) "Pharmacokinetic/pharmacodynamic modeling of IVIG effects in a murine model of immune thrombocytopenia," J. Pharm. Sci. 96(6):1625-1637.

Eymard et al. (2009) "[Antibodies in myasthenia gravis]," Rev. Neurol. (Paris). 165(2):137-143.—English abstract.

Federico et al. (2000) "Multifocal motor neuropathy improved by IVIg: randomized, double-blind, placebo-controlled study," Neurology. 55:1256-1262.

Flaherty et al. (Oct. 24, 2011) "Nonclinical evaluation of GMA161— an antihuman CD16 (Form) monoclonal antibody for treatment of autoimmune disorders in CD16 transgenic mice," Toxicological Sciences. 125(1):299-309.

Frusho et al. (1984) "High-dose intravenous gammaglobulin for Kawasaki disease," Lancet. 2:1055-1058.

Gan et al. (2009) "Analyses of the recycling receptor, FcRn, in live cells reveal novel pathways for lysosomal delivery," Traffic. 10:600-614.

Garcia et al. (2001) "Kinetics and thermodynamics of T cell receptor-autoantigen interactions in murine experimental autoimmune encephalomyelitis," Proc. Natl. Acad Sci. USA 98:6818-6823.

Ghetie et al. (1996) "Abnormally short serum half lives of IgGs in beta2-microglobulin deficient mice," Eur. J. mmunol. 26:690-696.

Ghetie et al. (1997) "Increasing the serum persistence of an IgG fragment by random mutagenesis," Nature Biotech. 15:637-640.

(56) References Cited

OTHER PUBLICATIONS

Ghetie et al. (2002) "Transcytosis and catabolism of antibody," Immunol. Res. 25(2):97-113.
Grevys et al. (Apr. 22, 2015) "Fc Engineering of Human IgG1 for Altered Binding to the Neonatal Fc Receptor Affects Fc Effector Functions," J Immunol. 194(11):5497-5508.
Guptill et al. (Aug. 11, 2016) "Effect of therapeutic plasma exchange on immunoglobulins in myasthenia gravis," Autoimmunity. 49(7):472-479.
Hansen et al. (2002) "Intravenous Immunoglobulin Mediates an Increase in Anti-Platelet Antibody Clearance via the FcRn Receptor," Thromb Haemost. 88:898-899.
Howard et al. (Apr. 30, 2013) "A randomized, double-blind, placebo-controlled phase II study of eculizumab in patients with refractory generalized myasthenia gravis," Muscle Nerve. 48(1):76-84.
Huang et al. (2005) "The central residues of a T cell receptor sequence motif are key determinants of autoantigen recognition in murine experimental autoimmune encephalomyelitis," Eur J. Immunol. 35:299-304.
Jain et al. (Aug. 20, 2012) "Fully recombinant IgG2a Fc multimers (stradomers) effectively treat collagen-induced arthritis and prevent idiopathic thrombocytopenic purpura in mice," Arthritis Research & Therapy 14:R192. pp. 1-12.
Kim et al. (1999) "Mapping of the site on human IgG1 for binding of the MHC class I related receptor, FcRn," Eur. J. Immunol. 29:2819-2825.
Law et al. (1997) "High-dose intravenous immune globulin and the response to splenectomy in patients with idiopathic thrombocytopenic purpura," N. Engl. J Med. 336:1494-1498.
Li et al. (2005) "Complete FcRn dependence for intravenous Ig therapy in autoimmune skin blistering diseases," J. Clin. Invest. 115(12):3440-3450.
Liu et al. (2007) "Amelioration of experimental autoimmune myasthenia gravis in rats by neonatal FcR blockade," J. Immunol. 178(8):5390-5398.
Liu et al. (2010) "Comparing the autoantibody levels and clinical efficacy of double filtration plasmapheresis, immunoadsorption, and intravenous immunoglobulin for the treatment of late-onset myasthenia gravis," Ther. Apher. Dial. 14(2): 153-160.
Low et al. (2009) "Inhibitors of the FcRn:IgG Protein-Protein Interaction," AAPS Journal. 11(3):432-434.
Lutterbach et al. (2007) "Lung cancer cell lines harboring Met gene amplification are dependent on Met for growth and survival," Cancer research. 67(5):2081-2088.
Massachusetts General Hospital (Dec. 10, 2012) "SuppreMol's SM101 shows a sustained clinical activity and a favorable saftey profile in Primary Immune Thrombocytopenia (ITP) patients," Press Release. Evaluate Ltd.
Medesan et al. (1997) "Delineation of the amino acid residues involved in transcytosis and catabolism of mouse IgG," J. Immunol. 158:2211-2217.
Mendell et al. (2001) "Randomized controlled trial of IVIg in untreated chronic inflammatory demyelinating polyradiculoneuropathy," Neurology. 56:445-449.
Meriggioli et al. (2009) "Autoimmune myasthenia gravis: emerging clinical and biological heterogeneity," The Lancet 8:475-490.
Mezo et al. (2008) "Reduction of IgG in nonhuman primates by a peptide antagonist of the neonatal Fc receptor FcRn," Proc. Natl. Acad Sci. USA. 105(7):2337-2342.
Mi et al. (2008) "Targeting the neonatal Fc receptor for antigen delivery using engineered Fc fragments," J. Immunol. 181:7550-7561.
Mohamed et al. (Jan. 7, 2013) "Massive intravascular haemolysis after high dose intravenous immunoglobulin therapy," British Journal of Haematology. 160:570.
Montoyo et al. (2009) "Conditional deletion of the MHC class I-related receptor FcRn reveals the sites of IgG homeostasis in mice," Proc. Natl. Acad. Sci. USA. 106:2788-2793.
Newburger et al. (2004) "Diagnosis, Treatment, and Long-Term Management of Kawasaki Disease: A Statement for Health Professionals From the Committee on Rheumatic Fever, Endocarditis, and Kawasaki Disease, Council on Cardiovascular Disease in the Young, American Heart Association," Pediatrics. 114:1708-1733.
Niknami et al. (Jun. 2013) "Beneficial effect of a multimerized immunoglobulin Fc in an animal model of inflammatory neuropathy (experimental autoimmune neuritis)," J. Peripher. Nerv. Syst. 18(2):141-52.
Ober et al. (2004) "Exocytosis of IgG as mediated by the receptor, FcRn: an analysis at the single-molecule level," Proc. Natl. Acad. Sci. USA. 101:11076-11081.
Alegre et al. (1994) "A Non-Activating "Humanized" Anti-CD3 Monoclonal Antibody Retains Immunosuppressive Properties in Vivo," Transplantation, 57(11):1537-1543.
Alipour-Faz et al. (2017) "A comparison between IVIG and plasma exchange as preparations before thymectomy in myasthenia gravis patients," Acta Neurol Belg, 117:245-249.
Andersen et al. (2012) "Structure-based mutagenesis reveals the albumin-binding site of the neonatal Fc receptor," Nat. Commun. 3:610. pp. 1-9.
Anonymous (2016) "Argenx announces initial results from Phase 1 multiple ascending dose (MAD) study of ARGX-113 in healthy volunteers—Argenx," 1 pg.
Argen-X N.V. (Apr. 24, 2014) "arGEN-X advances ARGX-113 into preclinical development for autoimmune disorders," Press Release. arGEN-X. Accessible on the Internet at URL: http://www.argen-x.com/en-GB/news-internal/argen-x-advances-argx-113-into-preclinical-devlopment-for-autoimmune-disorders/60. [Last Accessed Aug. 1, 2016].
Argen-X N.V. (Jun. 20, 2014) Prospectus for Public Offering of arGEN-X N.V.
Argen-X N.V. (Aug. 19, 2014) "arGEN-X announces positive preclinical results for ARGX-113," Press Release. EURONEXT. Accessible on the Internet at URL: https://www.euronext.com/nl/node/506652. [Last Accessed Aug. 1, 2016].
Armour et al. (1999) "Recombinant human IgG molecules lacking Fcgamma receptor I binding and monocyte triggering activities," Eur. J. Immunol. 29:2613-2624.
Chaudhury et al. (2003) "The major histocompatibility complex-related Fc receptor for IgG (FcRn) binds albumin and prolongs its lifespan," J. Exp. Med. 197(3):315-322.
Clarkson et al. (1986) "Treatment of Refractory Immune Thrombocytopenic Purpura with an Anti-Fcgamma-Receptor Antibody," New England Journal of Medicine. 314(9):1236-1239.
Duncan et al. (1988) "Localization of the binding site for the human high-affinity Fc receptor on IgG," Nature, 332:563-564.
Edelman et al. (1969) "The covalent structure of an entire gammaG immunoglobulin molecule," The Journal of Immunology, 63:5335-5342.
El-Salem et al. (2014) "Treatment of MuSK-Associated Myasthenia Gravis," Curr. Treat. Options Neurol., 16:283, 14 pages.
Genbank Database [online] (Jul. 2, 2016) "*Homo sapiens* Fc fragment of IgG receptor IIIa (FCGR3A), transcript variant 1, mRNA," Accession No. NM_000569. Accessible on the Internet at URL: http://www.ncbi.nlm.nih.gov/nuccore/NM_000569. [Last Accessed Aug. 19, 2016].
Grau (Sep. 21, 2011) "IgG core a-fucosylation and its impact on FcγRIIIa binding," Roche Glycart AG. In; MipTec2011, Basel, Switzerland.
Hanson (2014) "The role of the immunoglobulin G1 Fc N-glycan in FcγRIIIa affinity," Thesis for partial fulfillment of the degree of Master of Science. Iowa State University. Paper 14135.
Hutchins et al. (1995) "Improved biodistribution, tumor targeting, and reduced immunogenicity in mice with a gamma4 variant of Campath-1H," Proc. Natl. Acad. Sci., USA, 92:11980-11984.
Idusogie et al. (2000) "Mapping of the C1q Binding Site on Rituxan, a Chimeric Antibody with a Human IgG1 Fc," J. Immunol., 164:4178-4184.
Idusogie et al. (2001) "Engineered Antibodies with Increased Activity to Recruit Complement," J. Immunol., 166:2571-2575.
International Search Report and Written Opinion corresponding to International Patent Application PCT/EP2017/077966, dated Jan. 29, 2018.

(56) References Cited

OTHER PUBLICATIONS

International Search Report with Written Opinion corresponding to International Patent Application No. PCT/EP2018/084034, dated Feb. 18, 2019.
Jacob et al. (2012) "Presence and Pathogenic Relevance of Antibodies to Clustered Acetylcholine Receptor in Ocular and Generalized Myasthenia Gravis," Arch Neurol., 69(8):994-1001.
Jefferis et al. (1995) "Recognition sites on human IgG for Fcgamma receptors: the role of glycosylation," Immunology Letters, 44:111-117.
Jefferis et al. (1996) "Modulation of Fc(gamma)R and human complement activation by IgG3-core oligosaccharide interactions," Immunol. Lett. 54:101-104.
Jefferis et al. (2002) "Interaction sites on human IgG-Fc for FcgammaR: current models," Immunology Letters, 82:57-65.
Junghans et al. (1996) "The protection receptor for IgG catabolism is the beta2-microglobulin-containing neonatal intestinal transport receptor," Proc. Natl. Acad. Sci. USA. 93:5512-5516.
Junghans (1997) "Finally! The Brambell receptor (FcRB). Mediator of transmission of immunity and protection from catabolism for IgG," Immunologic Research. 16(1):29-57.
Kanda et al. (2006) "Comparison of biological activity among nonfucosylated therapeutic IgG1 antibodies with three different N-linked Fc oligosaccharides: the high-mannose, hybrid, and complex types," Glycobiol. 17(1):104-118.
Lund et al. (1991) "Human Fc gamma RI and Fc gamma RII interact with distinct but overlapping sites on human IgG," J. Immunol. 147:2657-2662.
Lund et al. (1992) "Multiple binding sites on the CH2 Domain of IgG for Mouse FcgammaRII," Molecular Immunology, 29(1):53-59.
Lund et al. (1995) "Oligosaccharide-protein interactions in IgG can modulate recognition by Fcgamma receptors," The FASEB Journal 9:115-119.
Lund et al. (1996) "Multiple interactions of IgG with its core oligosaccharide can modulate recognition by complement and human Fc gamma receptor I and influence the synthesis of its oligosaccharide chains," J. Immunol. 157:4963-4969.
MacCallum et al. (1996) "Antibody-antigen Interactions: Contact Analysis and Binding Site Topography," J. Mol. Biol., 262:732-745.
Meriggioli et al. (1999) "Autoimmune myasthenia gravis: emerging clinical and biological heterogeneity," The Lancet 8:475-490.
Morea et al. (2000) "Antibody Modeling: Implications for Engineering and Design," Methods, 20:267-279.
Nieswandt et al. (1999) "Acute systemic reaction and lung alterations induced by an antiplatelet integrin gpIIb/IIIa antibody in mice," Blood. 94:684-693.
Oshima et al. (1998) "Characterization of murine CD70 by molecular cloning and mAb," Int. Immunol. 10(4):517-526.
Pevzner et al. (2011) "Anti-LRP4 autoantibodies in AChR-and MuSK-antibody-negative myasthenia gravis," J. Neurol., 9 pages.
Presta et al. (2002) "Engineering therapeutic antibodies for improved function," Biochemical Society Transactions, 30(4):487-490.
Reddy et al. (2000) "Elimination of Fc Receptor-Dependent Effector Functions of a Modified IgG4 Monoclonal Antibody to Human CD4,"J. Immunol., 164:1925-1933.
Roopenian et al. (2003) "The MHC class I-like IgG receptor controls perinatal IgG transport, IgG homeostasis, and fate of IgG-Fc-coupled drugs," J. Immunology. 170:3528-3533.
Roux et al. (1998) "Comparisons of the Ability of Human IgG3 Hinge Mutants, IgM, IgE, and IgA2, to Form Small Immune Complexes: A Role for Flexibility and Geometry," The Journal of Immunology, 4083-4090.
Shields et al. (2001) "High Resolution Mapping of the Binding Site on Human IgG1 for FcgammaRI, FcgammaRII, FcgammaRIII, and FcRn and Design of IgG1 Variants with Improved Binding to the FcgammaR," The Journal of Biological Chemistry, 276(9):6591-6604.

Sockolosky et al. (2015) "The neonatal Fc receptor, FcRn, as a target for drug delivery and therapy," Advanced Drug Delivery Reviews, 91:109-124.
Task Force of the Medical Scientific Advisory Board of the Myasthenia Gravis Foundation of America, et al. (2000) "Myasthenia gravis," Neurology, 55:16-23.
Tramontano et al. (1990) "Framework Residue 71 is a Major Determinant of the Position and Conformation of the Second Hypervariable Region in the VH Domains of Immunoglobulins," J. Mol. Biol., 215:175-182.
Xu et al. (2000) "In Vitro Characterization of Five Humanized OKT3 Effector Function Variant Antibodies," Cellular Immunology, 200:16-26.
Yang et al., (2011) "Non-radioactive serological diagnosis of myasthenia gravis and clinical features of patients from Tianjin, China," Journal of Neurological Sciences, 301:71-76, 2011.
Zhang et al. (2012) "Autoantibodies to Lipoprotein-Related Protein in Patients With Double-Seronegative Myasthenia Gravis," Arch Neurol, 69(4):445-451.
Abdiche et al. (2015) "The neonatal Fc receptor (FcRn) binds independently to both sites of the IgG homodimer with identical affinity," mAbs, 7(2):331-343.
Imbach et al. (1981) "High-dose intravenous gammaglobulin for idiopathic thrombocytopenic purpura in childhood," The Lancet, 1228-1231.
Imbach et al. (1985) "Intravenous immunoglobulin versus oral corticosteroids in acute immune thrombocytopenic pupura in childhood," The Lancet, 464-468.
Imbach, Paul (2012) "Treatment of immune thrombocytopenia with intravenous immunoglobulin and insights for other diseases," Swiss Medical Weekly, 10 pages.
Martin et al. (2001) "Crystal Structure at 2.8 A of an FcRn/Heterodimeric Fc Complex Mechanism of pH-Dependent Binding," Molecular Cell, 7:867-877.
Newland et al. (1983) "High-dose intravenous IgG in adults with autoimmune thrombocytopenia," The Lancet, 84-87.
Sorde et al. (2017) "Massive immune response against IVIg interferes with response against other antigens in mice: A new mode of action?," PLoS ONE, 12(10):e0186046, 15 pages.
Ulrichts et al. (2018) "Neonatal Fc receptor antagonist efgartigimod safely and sustainably reduces IgGs in humans," J. Clin. Invest., 16 pages.
Ober et al. (2004) "Visualizing the site and dynamics of IgG salvage by the MHC Class I-related receptor, FcRn," J. Immunol. 172:2021-2029.
Patel et al. (2011) "Neonatal Fc receptor blockade by Fc engineering ameliorates arthritis in a murine model," J. Immunol. 187(2):1015-1022.
Prabhat et al. (2007) "Elucidation of intracellular recycling pathways leading to exocytosis of the Fc receptor, FcRn, by using multifocal plane microscopy," Proc. Natl. Acad. Sci. USA. 104:5889-5894.
Roopenian et al. (2007) "FcRn: the neonatal Fc receptor comes of age," Nat. Rev. Immunol. 7(9):715-725.
Schwab et al. (Mar. 2013) "Intravaneous immunoglobulin therapy: how does IgG modulate the immune system?" Nat. Rev. Immunol. 176(13).
Seidling et al. (2013) "Analysis of high-dose intravenous immunoglobulin therapy in 16 patients with refractory autoimmune blistering skin disease: high efficacy and no serious adverse events," Acta Derm Venereol. 93:346-349.
Semple (2010) "Animal models of immune thrombocytopenia (ITP)," Annals of Hematology. 89:37-44.
Sesarman et al. (2010) "The neonatal Fc receptor as therapeutic target in IgG-mediated autoimmune diseases," Cell. Mol. Life Sci. 67(15):2533-2550.
Sewell: Ed. (Jan. 22, 2010) First National Immunoglobulin Database Report. Department of Health.
Shelton (1999) "Acquired myasthenia gravis: what we have learned from experimental and spontaneous animal models," Veterinary Immunology and Immunopathology. 69:239-249.
Soliven (2012) "Autoimmune neuropathies: insights from animal models," Journal of the Peripheral Nervous System. 17:28-33.

(56) References Cited

OTHER PUBLICATIONS

Stamos et al. (2004) "Crystal structure of the HGF beta-chain in complex with the Sema domain of the Met receptor," EMBO J. 23(12):2325-2335.
Ulrichts et al. (May 2017) "ARGX-113: Towards a Safe and Selective Elimination of Pathogenic Autoantibodies," 13th International Conference on Myasthenia Gravis and Related Disorders, May 15-17, 2017. New York, New York. Poster Presentation.
Vaccaro et al. (2005) "Engineering the Fc region of immunoglobulin G to modulate in vivo antibody levels," Nat. Biotechnol. 23(10):1283-1288.
Vaccaro et al. (2006) "Divergent activities of an engineered antibody in murine and human systems have implications for therapeutic antibodies" Proc. Natl. Acad. Sci. USA. 103(49):18709-18714.
Van Der Meche et al. (1992) "A randomized trial comparing intravenous immune globulin and plasma exchange in Guillain—Barre syndrome. Dutch Guillain-Barre Study Group," N. Engl. J. Med. 326:1123-1129.
Wani et al. (2006) "Familial hypercatabolic hypoproteinemia caused by deficiency of the neonatal Fc receptor, FcRn, due to a mutant beta2-microglobulin gene," Proc. Natl. Acad. Sci. USA. 103(13):5084-5989.
Woods et al. (1984) "Autoantibodies against platelet glycoprotein lb in patients with chronic immune thrombocytopenic purpura," Blood 64:156-160.
Zhou et al. (2003) "Generation of mutated variants of the human form of the MHC class I-related receptor, FcRn, with increased affinity for mouse immunoglobulin G," J. Mol. Biol. 332:901-913.
Zhou et al. (2005) "Conferring the binding properties of the mouse MHC Class Irelated receptor, FcRn, onto the human ortholog by sequential rounds of site-directed mutagenesis," J. Mol. Biol. 345:1071-1081.
Zinman et al. (2007) "IV immunoglobulin in patients with myasthenia gravis: a randomized controlled trial," Neurology 68:837-841.
International Preliminary Report on Patentability corresponding to International Patent Application No. PCT/EP2013/068399, dated Mar. 10, 2015.
International Preliminary Report on Patentability corresponding to International Patent Application No. PCT/US2014/072087, dated Jun. 28, 2016.
International Search Report corresponding to International Patent Application No. PCT/EP2013/068399, dated Apr. 9, 2014.
International Search Report with Written Opinion corresponding to International Patent Application No. PCT/US2014/072087, dated May 4, 2015.
Written Opinion corresponding to International Patent Application No. PCT/EP2013/068399, dated Apr. 14, 2014.
"Anthony et al., Apr. 18, 2008, Science, 320(5874): 373-376", Document D14 submitted with Notice of Opposition for European Patent No. 3087095 (Application No. 14827372.5), dated May 7, 2020.
"arGEN-X advances ARGX-113 into preclinical development for autoimmune disorders, Apr. 24, 2014", Document D38 submitted with Notice of Opposition for European Patent No. 3087095 (Application No. 14827372.5), dated May 7, 2020.
"arGEN-X Announces Positive Preclinical Results for ARGX-113, Aug. 19, 2014", Document D39 submitted with Notice of Opposition for European Patent No. 3087095 (Application No. 14827372.5), dated May 7, 2020.
"Assignment submission for U.S. Appl. No. 61/920,547 confirming change of legal form of arGEN-X B.V. to arGEN-X N.V. on May 28, 2014", Document D30 submitted with Notice of Opposition for European Patent No. 3087095 (U.S. Appl. No. 61/920,547), dated May 7, 2020.
"Auxiliary Request 1—Annotated Version" for European Patent No. 3087095 (Application No. 14827372.5), dated Oct. 28, 2020, 5 pages.
"Auxiliary Request 1—Clean Version" for European Patent No. 3087095 (Application No. 14827372.5), dated Oct. 28, 2020, 5 pages.
"Auxiliary Request 2—Annotated Version" for European Patent No. 3087095 (Application No. 14827372.5), dated Oct. 28, 2020, 5 pages.
"Auxiliary Request 2—Clean Version" for European Patent No. 3087095 (Application No. 14827372.5), dated Oct. 28, 2020, 4 pages.
"Blumberg & Lencer, Oct. 2005, Nat Biotechnol., 23(10): 1232-1234", Document D03 submitted with Notice of Opposition for European Patent No. 3087095 (Application No. 14827372.5), dated May 7, 2020.
"Bruhns et al., Apr. 2003, Immunity, 18(4): 573-571", Document D16 submitted with Notice of Opposition for European Patent No. 3087095 (Application No. 14827372.5), dated May 7, 2020.
"Brych et al., Feb. 2010, J Pharm Sci., 99(2): 764-781", Document D37 submitted with Notice of Opposition for European Patent No. 3087095 (Application No. 14827372.5), dated May 7, 2020.
"Carter, May 2006, Nat Rev immunol., 6(5): 343-357", Document D22 submitted with Notice of Opposition for European Patent No. 3087095 (Application No. 14827372.5), dated May 7, 2020.
"Challa et al., Sep.-Oct. 2013, MAbs, 5(5): 655-659", Document D10 submitted with Notice of Opposition for European Patent No. 3087095 (Application No. 14827372.5), dated May 7, 2020.
"Corrected Filing Receipt for U.S. Appl. No. 61/920,547 dated Apr. 16, 2015", Document D27 submitted with Notice of Opposition for European Patent No. 3087095 (U.S. Appl. No. 61/920,547), dated May 7, 2020.
"Corrected Filing Receipt for U.S. Appl. No. 61/920,547 dated Apr. 18, 2014", Document D26 submitted with to Notice of Opposition for European Patent No. 3087095 (U.S. Appl. No. 61/920,547), dated May 7, 2020.
"Cover Letter to the European Patent Office" for European Patent No. 3087095 (Application No. 14827372.5), dated Oct. 28, 2020, 1 page.
"Dall'Acqua et al., Nov. 1, 2002, J Immunol., 169(9): 5171-5180", Document D21 submitted with Notice of Opposition for European Patent No. 3087095 (Application No. 14827372.5), dated May 7, 2020.
"Debre et al., Oct. 16, 1993, Lancet, 342: 945-949", Document D12 submitted with Notice of Opposition for European Patent No. 3087095 (Application No. 14827372.5), dated May 7, 2020.
"Declaration of Pieter Spuijbroek", Document D42 submitted with Reply to Notice of Opposition for European Patent No. 3087095 (Application No. 14827372.5), dated Oct. 28, 2020, 5 pages.
"Dimitrov, Jan.-Feb. 2009, MAbs, 1(1): 26-28", Document D20 submitted with Notice of Opposition for European Patent No. 3087095 (Application No. 14827372.5), dated May 7, 2020.
"EP 1896503 Amended Claims and Response submitted Feb. 23, 2014 during prosecution of the application which led to grant of D1", Document D02a submitted with Notice of Opposition for European Patent No. 3087095 (Application No. 14827372.5), dated May 7, 2020.
"EP 1896503 B1 dated Oct. 29, 2014", Document D01 submitted with Reply to Notice of Opposition for European Patent No. 3087095 (Application No. 14827372.5), dated May 7, 2020.
"EP 3087095 B1 dated Aug. 7, 2019" submitted with Notice of Opposition for European Patent No. 3087095 (Application No. 14827372.5), dated May 7, 2020.
"Filing Receipt for U.S. Appl. No. 61/920,547 dated Jan. 21, 2014", Document D25 submitted with Notice of Opposition for European Patent No. 3087095 (U.S. Appl. No. 61/920,547), dated May 7, 2020.
"Gan et al., May 2009, Traffic, 10(5): 600-614", Document D08 submitted with Notice of Opposition for European Patent No. 3087095 (Application No. 14827372.5), dated May 7, 2020.
"Goh and Ng, Sep. 2018, Crit Rev Biotechnol., 38(6): 851-867", Document D19 submitted with Notice of Opposition for European Patent No. 3087095 (Application No. 14827372.5), dated May 7, 2020.

(56) References Cited

OTHER PUBLICATIONS

"Gómez-Guerrero et al., Feb. 15, 2000, J Immunol., 164(4): 2092-2101", Document D15 submitted with Notice of Opposition for European Patent No. 3087095 (Application No. 14827372.5), dated May 7, 2020.
"Inventor Assignment of U.S. Appl. No. 61/920,547 to arGEN-X B.V. executed Oct. 31, 2014 and Nov. 4, 2014", Document D29 submitted with Notice of Opposition for European Patent No. 3087095 (U.S. Appl. No. 61/920,547), dated May 7, 2020.
"Inventor Assignment of U.S. Appl. No. 61/920,547 to The Board of Regents of the University of Texas System executed Dec. 23, 2014", Document D28 submitted with Notice of Opposition for European Patent No. 3087095 (U.S. Appl. No. 61/920,547), dated May 7, 2020.
"Jefferis and Lefranc, Jul.-Aug. 2009, MAbs, 1(4): 332-338", Document D35 submitted with Notice of Opposition for European Patent No. 3087095 (Application No. 14827372.5), dated May 7, 2020.
"Kaneko et al., Aug. 4, 2006, Science, 313(5787): 670-673", Document D17 submitted with Notice of Opposition for European Patent No. 3087095 (Application No. 14827372.5), dated May 7, 2020.
"Main Request—Annotated Version" for European Patent No. 3087095 (Application No. 14827372.5), dated Oct. 28, 2020, 5 pages.
"Main Request—Clean Version" for European Patent No. 3087095 (Application No. 14827372.5), dated Oct. 28, 2020, 5 pages.
"Notice of Opposition" to European Patent No. 3087095 (Application No. 14827372.5), dated May 7, 2020, 47 pages.
"Online Filing Acknowledgement for Notice of Opposition" for European Patent No. 3087095 (Application No. 14827372.5), dated May 7, 2020, 3 pages.
"Online Filing Acknowledgement for Reply to Notice of Opposition" for European Patent No. 3087095 (Application No. 14827372.5), dated Oct. 28, 2020, 2 pages.
"Patel et al., Jul. 15, 2011, J Immunol., 187(2): 1015-1022", Document D09 submitted with Notice of Opposition for European Patent No. 3087095 (Application No. 14827372.5), dated May 7, 2020.
"PCT Request for as filed for PCT/US2014/072087 on Dec. 23, 2014", Document D34 submitted with Notice of Opposition for European Patent No. 3087095 (Application No. 14827372.5), dated May 7, 2020.
"Proof of Employment for Inventor/Applicant Sally Ward", Document D40 submitted with Reply to Notice of Opposition for European Patent No. 3087095 (Application No. 14827372.5), dated Oct. 28, 2020, 1 page.
"Putnam and Miyake, Apr. 1958, J Biol Chern, 231(2):671-684", Document D33 submitted with Notice of Opposition for European Patent No. 3087095 (Application No. 14827372.5), dated May 7, 2020.
"Pyzik et al., Jul. 10, 2019, Front Immunol., 10: 1540", Document D31 submitted with Notice of Opposition for European Patent No. 3087095 (Application No. 14827372.5), dated May 7, 2020.
"Reply to Notice of Opposition" for European Patent No. 3087095 (Application No. 14827372.5), dated Oct. 28, 2020, 35 pages,.
"Rule 90101 of the Rules and Regulations of the Board of Regents of the University of Texas System governing intellectual property" dated Feb. 27, 2012, Document D41 submitted with Reply to Notice of Opposition for European Patent No. 3087095 (Application No. 14827372.5), on Oct. 28, 2020, 21 pages.
"Samuelsson et al., Jan. 19, 2001, Science, 291(5503): 484-486", Document D13 submitted with Notice of Opposition for European Patent No. 3087095 (Application No. 14827372.5), dated May 7, 2020.
"Schwab and Nimmerjahn, Mar. 2013, Nat Rev Immunol., 13(3): 176-189", Document D11 submitted with Notice of Opposition for European Patent No. 3087095 (Application No. 14827372.5), dated May 7, 2020.
"Sequence alignment of Seq ID No. 22 from D6 and Seq ID Nos. 1,2, and 3 from the Patent", Document D32 submitted with Notice of Opposition for European Patent No. 3087095 (Application No. 14827372.5), dated May 7, 2020.
"Sequence Alignment of Seq ID Nos. 1-3 from Patent and corresponding portion of Uniprot ID: P01857", Document D24 submitted with Notice of Opposition for European Patent No. 3087095 (Application No. 14827372.5), dated May 7, 2020.
"Shields et al., Mar. 2, 2001, J Biol Chern., 276(9): 6591-6604", Document D23 submitted with Notice of Opposition for European Patent No. 3087095 (Application No. 14827372.5), dated May 7, 2020.
"Ulrichts et al., Oct. 1, 2018, J Clin Invest., 128(10): 4372-4386", Document D18 submitted with Notice of Opposition for European Patent No. 3087095 (Application No. 14827372.5), dated May 7, 2020.
"UniProtKB—P01857 (IGHG1_HUMAN)", Document D43 submitted with Reply to Notice of Opposition for European Patent No. 3087095 (Application No. 14827372.5), dated Oct. 28, 2020, 6 pages.
"Vacarro et al., Dec. 2006, Proc Natl Acad Sci USA, 103(49): 18709-18714", Document D07 submitted with Notice of Opposition for European Patent No. 3087095 (Application No. 14827372.5), dated May 7, 2020.
"Vaccarro et al., Oct. 2005, Nat Biotechnol., 23(10): 1283-1288", Document D04 submitted with Notice of Opposition for European Patent No. 3087095 (Application No. 14827372.5), dated May 7, 2020.
"Ward & Ober, 2009, Chapter 4, Adv. Immunol., 103: 77-115", Document D05 submitted with Notice of Opposition for European Patent No. 3087095 (Application No. 14827372.5), dated May 7, 2020.
"Weiner and Carter, May 2005, 23(5): 556-557", Document D36 submitted with Notice of Opposition for European Patent No. 3087095 (Application No. 14827372.5), dated May 7, 2020.
"WO 2006/130834 A2 dated Dec. 7, 2006", Document D02 submitted with Notice of Opposition for European Patent No. 3087095 (Application No. 14827372.5), dated May 7, 2020.
"WO 2013/074598 A1 dated May 23, 2013", Document D06 submitted with Notice of Opposition for European Patent No. 3087095 (Application No. 14827372.5), dated May 7, 2020.
"WO 2015/100299 A1 dated Jul. 2, 2015" submitted with Notice of Opposition for European Patent No. 3087095 (Application No. 14827372.5), dated May 7, 2020.
Anonymous (2016) "Argenx announces initial results from Phase 1 multiple ascending dose (MAD) study of ARGX-113 in healthy volunteers—Argenx," 3 pgs.
Balighi et al., "Comparing early and late treatments with rituximab in pemphigus vulgaris: which one is better?", Archives of Dermatological Research, Dec. 1, 2018, 311(1): 63-69.
Bussel et al. (Feb. 1, 2015) "Long-term use of the thrombopoietin-mimetic romiplostim in children with severe chronic immune thrombocytopenia (ITP): Romiplostim in Pediatric ITP" Pediatric Blood and Cancer, 62(2): 208-213.
Bussel et al. (Jul. 7, 2011) "A Randomized, Double-Blind Study of Romiplostim to Determine its Safety and Efficacy in Children with Immune Thrombocytopenia", Blood, 118(1): 28-36.
ClinicalTrials.gov (Apr. 6, 2017) "A Study to Evaluate the Safety, Efficacy, and Pharmacokinetics of ARGX-113 in Patients with ITP", ClinicalTrials.gov Identifier: NCT03102593.
Clinicaltrials.gov, "A Study to Evaluate the Safety, PD, PK and Efficacy of ARGX-113 in Patients with Pemphigus", ClinicalTrials.gov Identifier NCT03334058, November?, 2017, 8 pages.
Clinicaltrials.gov, "A Study to Evaluate the Safety, PD, PK and Efficacy of ARGX-113 in Patients with Pemphigus", ClinicalTrials.gov Identifier NCT04598477, Oct. 22, 2020, 10 pages.
Combined Search and Examination Report for Great Britain Application No. GB1617270.2, dated Aug. 3, 2017, 6 pages.
Daugherty et al., "Formulation and delivery issues for monoclonal antibody therapeutics", Adv Drug Deliv Rev., Aug. 7, 2006, 58(5-6): 686-706.
De Haard et al. (Dec. 4, 2016) "Advancing ARGX-113 and ARGX-110 to Clinical Proof of Concept", pp. 1-575.

(56) References Cited

OTHER PUBLICATIONS

Dick Jr. et al., "C-Terminal Lysine Variants in Fully Human Monoclonal Antibodies: Investigation of Test Methods and Possible Causes", Biotechnology and Bioengineering, 2008, vol. 100, No. 6, pp. 1132-1143.

Eddleston et al. (Dec. 7, 2017) "Blockade of the Neonatal Fc Receptor (FcRn) Represents an Effective Mechanism for the Removal of Pathogenic Autoantibodies in Primary Immune Thrombocytopenia", Database accession No. PREV201900186122 abstract & Blood, 130(Suppl. 1): 230, Database Biosis [Online] Biosciences Information Service, XP002794883.

Gilhus et al. (2011) "Myasthenia Gravis: A Review of Available Treatment Approaches," Autoimmune Diseases, Article ID 847393, 6 pages.

Howard et al., "Randomized phase 2 study of FcRn antagonist efgartigimod in generalized myasthenia gravis", Neurology, 2019, vol. 92, No. 23, pp. 1-8.

Imbach et al. (2009) "Intravenous immunoglobulins induce potentially synergistic immunomodulations in autoimmune disorders", Vox Sanguinis, 10 pages.

International Preliminary Report on Patentability for PCT International Patent Application No. PCT/IB2019/054786, dated Dec. 8, 2020.

International Preliminary Report on Patentability for PCT International Patent Application No. PCT/IB2016/000398, dated Sep. 12, 2017.

International Search Report and Written Opinion in related PCT Application No. PCT/IB2019/054786, dated Dec. 18, 2109, 27 pages.

International Search Report with Written Opinion for PCT International Patent Application No. PCT/IB2016/000398, dated Aug. 22, 2016.

International Search Report with Written Opinion for PCT International Patent Application No. PCT/EP2020/065716, dated Sep. 14, 2020.

International Search Report with Written Opinion for PCT International Patent Application No. PCT/EP2021/050275, dated Apr. 8, 2021.

Jaretzkl et al., "Myasthenia gravis: recommendations for clinical research standards. Task Force of the Medical Scientific Advisory Board of the Myasthenia Gravis Foundation of America", Ann Thorac Surg., Jul. 2000, 70(1): 327-334.

Kabat et al., "Unusual Distributions of amino Acids in Complementarity-determining (Hypervariable) Segments of Heavy and Light Chains of Immunoglobulins and Their Possible Roles in Specificity of Antibody-combining Sites", The Journal of Biological Chemistry, Oct. 1, 1977, 252(19): 6609-6616.

Kang et al., "Rapid Formulation Development for Monoclonal Antibodies", BioProcess International, Apr. 12, 2016, retrieved from url:https://bioprocessintl.com/manufacturing/formulation/rapid-formulation-development-for-monoclonal-antibodies/.

Robak et al., "Phase II, Multiple-Dose Study of Anti-FcRn Antibody, Rozanolixizumab (UCB7665), in Patients with Primary Immune Thrombocytopenia: Interim Analysis", Blood, Dec. 7, 2017, 130(Suppl. 1): 15, 59th Annual Meeting of the American-Society-of-Hematology, Dec. 9-12, 2017.

Shang et al., "Modular protein expression by RNA trans-splicing enables flexible expression of antibody formats in mammalian cells from a dual-host phage display vector", Protein Engineering, Design & Selection, 2015, vol. 28, No. 10, pp. 437-444.

Swiercz et al. (May 27, 2014) "Use of Fc-engineered antibodies as clearing agents to increase contrast during PET", J. Nucl. Med., 55: 1204-1207.

Swiss Webster Mice, by TACONIC, Aug. 23, 2018, pp. 1-7.

Ulrichts et al., "ARGX-113, a Novel Fc-Based Approach for Antibody-Induced Pathologies Such as Primary Immune Thrombocytopenia", Blood, vol. 128, No. 22, Dec. 2016, p. 4919, 58th annual Meeting and Exposition of the American-Society-of-Hematology; San Diego, CA, Dec. 3-6, 2016.

Wang et al., "Protein aggregation and its inhibition on biopharmaceutics", International Journal of Pharmaceutics, Jan. 31, 2005, 289(1-2): 1-30.

Ying et al. (2012) "Soluble Monomeric IgG1 Fc," The Journal of Biological Chemistry, 287(23):19399-19408.

Ying et al. (2013) "Engineered Soluble Monomeric IgG1 CH3 Domain," The Journal of Biological Chemistry, 288 (35):25154-25164.

U.S. Appl. No. 14/580,771, filed Dec. 23, 2014, 2015/0218239, Aug. 6, 2015, U.S. Pat. No. 10,316,073, Jun. 11, 2019, Peter Ulrichts.

U.S. Appl. No. 15/821,104, filed Nov. 22, 2017, 2018/0179258, Jun. 28, 2018, Peter Ulrichts.

U.S. Appl. No. 15/064,195, filed Mar. 8, 2016, 2016/0264669, Sep. 15, 2016, Peter Ulrichts.

U.S. Appl. No. 16/213,422, filed Dec. 7, 2018, 2019/0194277, Jun. 27, 2019, Johannes de Haard.

U.S. Appl. No. 16/893,863, filed Jun. 5, 2020, 2020/0399363, Dec. 24, 2020, Filip Borgions.

U.S. Appl. No. 16/435,166, filed Jun. 7, 2019, 2020/0024344, Aug. 23, 2020, Hans de Haard.

PCT/IB2019/054786, filed Jun. 7, 2019, WO 2019/234713, Dec. 12, 2019, Hans de Haard.

U.S. Appl. No. 17/144,481, filed Jan. 8, 2021, 2021/0236596, Aug. 5, 2021, Peter Verheesen.

Bussel et al. 2007 "Eltrombopag for the treatment of chronic idiopathic thrombocytopenic purpura," N Engl J Med. 357(22): 2237-47.

Janeway et al. 2005 "Immunobiology: the immune system in health and disease" 6th Garland Science, New York.

Khan et al. 2017 "Clinical Practice Updates in the Management Of Immune Thrombocytopenia," P & T. 42(12): 756-763.

Newland et al. 2020 "Phase 2 study of efgartigimod, a novel FcRn antagonist, in adult patients with primary immune thrombocytopenia," Am J Hematol. 95(2): 178-187.

* cited by examiner

FCRN ANTAGONISTS AND METHODS OF USE

RELATED APPLICATIONS

This application is a division of U.S. patent application Ser. No. 14/580,771, filed Dec. 23, 2014, which claims priority to U.S. Provisional Patent Application Ser. No. 61/920,547, filed Dec. 24, 2013, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Nov. 22, 2017, is named 597068_AGX5-019DV_Sequence_Listing.txt and is 6,602 bytes in size.

GOVERNMENT RIGHTS

This invention was made with government support under Grant No. R01 AR 56478 awarded by the National Institutes of Health. The government has certain rights in the invention.

BACKGROUND

Immunoglobulin gamma (IgG) antibodies play a key role in the pathology of many disorders, such as autoimmune diseases, inflammatory diseases, and disorders in which the pathology is characterized by over-expression of IgG antibodies (e.g., hypergammaglobulinemia) (see e.g. Junghans, Immunologic Research 16 (1):29 (1997)).

The half-life of IgG in the serum is prolonged relative to the serum half-life of other plasma proteins (Roopenian et al., J. Immunology 170:3528 (2003); Junghans and Anderson, Proc. Natl. Acad. Sci. USA 93:5512 (1996)). This long half-life is due, in part, to the binding of the Fc region of IgG to the Fc receptor, FcRn. Although FcRn was originally characterized as a neonatal transport receptor for maternal IgG, it also functions in adults to protect IgG from degradation. FcRn binds to pinocytosed IgG and protects the IgG from transport to degradative lysosomes by recycling it back to the extracellular compartment. This recycling is facilitated by the pH dependent binding of IgG to FcRn, where the IgG/FcRn interaction is stronger at acidic endosomal pH than at extracellular physiological pH.

When the serum concentration of IgG reaches a level that exceeds available FcRn molecules, unbound IgG is not protected from degradative mechanisms and will consequently have a reduced serum half-life. Thus, inhibition of IgG binding to FcRn reduces the serum half-life of IgG by preventing IgG endosomal recycling of IgG. Accordingly, agents that antagonize the binding of IgG to FcRn may be useful for regulating, treating or preventing antibody-mediated disorders, such as autoimmune diseases, inflammatory diseases, etc. One example of a method of antagonizing IgG Fc binding to FcRn involves the generation of blocking antibodies to FcRn (see e.g WO2002/43658). Peptides have also been identified that bind to and antagonize FcRn function (see e.g. U.S. Pat. Nos. 6,212,022 and 8,101,186). In addition, full-length IgG antibodies comprising variant Fc receptors with enhanced FcRn binding and decreased pH dependence have also been identified that antagonize FcRn binding to IgG (see e.g. U.S. Pat. No. 8,163,881). However, there is a need in the art for improved agents that antagonize FcRn binding to IgG for use in the treatment of antibody-mediated disorders.

SUMMARY

The present disclosure provides novel FcRn antagonist compositions. These compositions generally comprise a variant Fc region, or FcRn-binding fragment thereof, that binds specifically to FcRn with increased affinity and reduced pH dependence relative to the native Fc region. The invention is based, in part, on the surprising finding that an isolated variant Fc region (e.g., a variant Fc region comprising the amino acids Y, T, E, K, F, and Y at EU positions (EU numbering) 252, 254, 256, 433, 434, and 436 respectively) is a more efficacious FcRn antagonist in vivo than a full-length antibody comprising that variant Fc region. The FcRn antagonist compositions of the present disclosure are particularly useful for reducing the serum levels of Fc-containing agents (e.g., antibodies and immunoadhesins). Accordingly, the instant disclosure also provides methods of treating antibody-mediated disorders (e.g. autoimmune diseases) using the FcRn antagonist compositions disclosed herein. Also provided are nucleic acids encoding the FcRn antagonist compositions, recombinant expression vectors and host cells for making the FcRn antagonist compositions, and pharmaceutical compositions comprising the FcRn antagonist compositions.

The FcRn antagonists disclosed herein are particularly advantageous over previously described FcRn antagonist compositions and known treatments for antibody-mediated disorders. For example, the FcRn antagonists disclosed herein are smaller and more potent than intravenous gamma globulin (IVIG), the current treatment for many antibody-mediated disorders. Accordingly, the effective dose of the disclosed FcRn antagonists can be far less than that of IVIG. Moreover, IVIG is isolated and purified from human donors and, as a consequence, suffers from considerable batch-batch variation. The FcRn antagonists compositions disclosed herein can be recombinantly produced or chemically synthesized and, therefore, are far more homogeneous. As demonstrated herein, the FcRn antagonists disclosed herein are also surprisingly more efficacious than full-length IgG antibodies comprising variant Fc receptors, such as set forth in Vaccaro et al., Nature Biotech 23(9) 1283-1288 (1997).

Accordingly, in one aspect, the instant disclosure provides an isolated FcRn antagonist comprising a variant Fc region or FcRn-binding fragment thereof, wherein the Fc region or fragment comprises the amino acids Y, T, E, K, F, and Y at EU positions 252, 254, 256, 433, 434, and 436 respectively, and wherein the FcRn antagonist is not a full-length antibody.

In certain embodiments, the FcRn antagonist does not comprise an antibody variable region or a CH1 domain. In certain embodiments, the FcRn antagonist does not comprise a free cysteine residue. In certain embodiments, the Fc region is an IgG Fc region (e.g., a human IgG Fc region). In certain embodiments, the Fc region is an IgG1 Fc region (e.g., a human IgG1 Fc region). In certain embodiments, the Fc region is a chimeric Fc region.

In certain embodiments, the FcRn antagonist comprises the variant Fc region amino acid sequence set forth in SEQ ID NO:1. In certain embodiments, the FcRn antagonist comprises a variant Fc region wherein the amino acid sequence of the Fc domains of the variant Fc region consists of the amino acid sequence set forth in SEQ ID NO: 1, 2, or 3. In certain embodiments, the FcRn antagonist consists of a variant Fc region wherein the amino acid sequence of the Fc domains of the variant Fc region consists of the amino acid sequence set forth in SEQ ID NO: 2.

In certain embodiments, the FcRn antagonist comprises a variant Fc region that has altered (increased or decreased) affinity for an Fc receptor relative to the affinity of a wild-type IgG1 Fc region for the Fc gamma receptor. In certain embodiments, the variant Fc has increased affinity for CD16a.

In certain embodiments, the FcRn antagonist comprises a variant Fc region that does not comprise an N-linked glycan at EU position 297. In certain embodiments, the FcRn antagonist comprises a variant Fc region that comprises an afucosylated N-linked glycan at EU position 297. In certain embodiments, the FcRn antagonist comprises a variant Fc region that comprises an N-linked glycan having a bisecting GlcNac at EU position 297.

In certain embodiments, the FcRn antagonist comprises a variant Fc region linked to a half-life extender. In certain embodiments, the half-life extender is polyethylene glycol or human serum albumin. In certain embodiments, the instant disclosure provides an FcRn antagonist composition comprising a plurality of FcRn antagonist molecules disclosed herein, wherein at least 50% (optionally, at least 60, 70, 80, 90, 95, or 99%) of the molecules comprise a variant Fc region, or FcRn-binding fragment thereof, having an afucosylated N-linked glycan. In certain embodiments, the instant disclosure provides an FcRn antagonist composition comprising a plurality of FcRn antagonist molecules disclosed herein, wherein at least 50% (optionally, at least 60, 70, 80, 90, 95, or 99%) of the molecules comprise a variant Fc region, or FcRn-binding fragment thereof, comprising an N-linked glycan having a bisecting GlcNac.

In certain embodiments, the instant disclosure provides an FcRn antagonist composition comprising a plurality of FcRn antagonist molecules as disclosed herein, wherein greater than 95% the of the FcRn antagonist molecules in the composition are monomers (e.g., greater than 95, 96, 97, 98, 99, 99.1, 99.2, 99.3, 99.4, 99.5, 99.6, 99.7, 99.8, 99.9%).

In certain embodiments, the instant disclosure provides an FcRn antagonist composition comprising a plurality of FcRn antagonist molecules disclosed herein, wherein less than 5% the of the FcRn antagonist molecules in the composition are present in aggregates, (e.g., less than 5, 4, 3, 2, 1, 0.9, 0.8, 0.7, 0.6, 0.5, 0.4, 0.3, 0.2, 0.1%).

In certain embodiments, the instant disclosure provides an FcRn antagonist composition comprising a plurality of FcRn antagonist molecules disclosed herein, wherein the composition is substantially free of FcRn antagonist molecule degradation products.

In another aspect, the instant disclosure provides pharmaceutical compositions comprising an FcRn antagonist or FcRn antagonist composition disclosed herein and a pharmaceutically acceptable carrier or excipient.

In another aspect, the instant disclosure provides a method of inhibiting FcRn function in a subject, the method comprising administering to the subject an effective amount of an FcRn-antagonist composition disclosed herein.

In another aspect, the instant disclosure provides a method of reducing the serum levels of an Fc-containing agent in subject that has been administered the Fc-containing agent, the method comprising administering to subject an effective amount of an FcRn-antagonist composition disclosed herein. In certain embodiments, the Fc-containing agent is an antibody or immunoadhesin. In certain embodiments, the Fc-containing agent is a therapeutic or diagnostic agent. In certain embodiments, the Fc-containing agent is an imaging agent. In certain embodiments, the Fc-containing agent is an antibody drug conjugate.

In another aspect, the instant disclosure provides a method of treating an antibody-mediated disorder in a subject, the method comprising administering to the subject an effective amount of an FcRn-antagonist composition disclosed herein. In certain embodiments, the antibody-mediated disorder is hyperglobulinemia. In certain embodiments, the antibody-mediated disorder is a disease or disorder that is treatable using intravenous immunoglobulin (IVIG). In certain embodiments, the antibody-mediated disorder is a disease or disorder that is treatable using plasmapheresis and/or immunoadsorption.

In certain embodiments, the antibody-mediated disorder is an autoimmune disease. In certain embodiments, the autoimmune disease is selected from the group consisting of allogenic islet graft rejection, alopecia areata, ankylosing spondylitis, antiphospholipid syndrome, autoimmune Addison's disease, Alzheimer's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac sprue-dermatitis, chronic fatigue immune disfunction syndrome, chronic inflammatory demyelinating polyneuropathy (CIDP), Churg-Strauss syndrome, cicatrical pemphigoid, CREST syndrome, cold agglutinin disease, Crohn's disease, dermatomyositis, dilated cardiomyopathy, discoid lupus, epidermolysis bullosa acquisita, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic membranous neuropathy, idiopathic pulmonary fibrosis, idiopathic thrombocytopenic purpura (ITP), IgA neuropathy, IgM polyneuropathies, immune mediated thrombocytopenia, juvenile arthritis, Kawasaki's disease, lichen planus, lichen sclerosus, lupus erythematosus, Meniere's disease, mixed connective tissue disease, mucous membrane pemphigoid, multiple sclerosis, type 1 diabetes mellitus, Multifocal motor neuropathy (MMN), myasthenia gravis, paraneoplastic bullous pemphigoid, pemphigoid gestationis, pemphigus vulgaris, pemphigus *foliaceus*, pernicious anemia, polyarteritis *nodosa*, polychrondritis, polyglandular syndromes, polymyalgia rheumatica, polymyositis and dermatomyositis, primary agammaglobinulinemia, primary biliary cirrhosis, psoriasis, psoriatic arthritis, relapsing polychondritis, Reynaud's phenomenon, Reiter's syndrome, rheumatoid arthritis, sarcoidosis, scleroderma, Sjögren's syndrome, solid organ transplant rejection, stiff-man syndrome, systemic lupus erythematosus, Takayasu arteritis, toxic epidermal necrolysis (TEN), Stevens Johnson syndrome (SJS), temporal arteritis/giant cell arteritis, thrombotic thrombocytopenia purpura, ulcerative colitis, uveitis, dermatitis herpetiformis vasculitis, anti-neutrophil cytoplasmic antibody-associated vasculitides, vitiligo, and Wegner's granulomatosis.

In certain embodiments, the autoimmune disease is an autoimmune channelopathy. In certain embodiments, the channelopathy is selected from the group consisting of autoimmune limbic encephalitis, epilepsy, neuromyelitis optica, Lambert-Eaton myasthenic syndrome, myasthenia gravis, anti-N-Methyl-D-aspartate (NMDA) receptor encephalitis, anti-α-Amino-3-hydroxy-5-methyl-4-isoxazolepropionic acid (AMPA) receptor encephalitis, Morvan syndrome, neuromyotonia, pediatric autoimmune neuropsychiatric disorders associated with streptococcal infection (PANDAS), and Glycine receptor antibody-associated disorder.

In certain embodiments, the FcRn antagonist is administered to the subject simultaneously or sequentially with an additional therapeutic agent. In certain embodiments, the additional therapeutic agent is an anti-inflammatory agent. In certain embodiments, the additional therapeutic agent is rituximab, daclizumab, basiliximab, muronomab-cd3, infliximab, adalimumab, omalizumab, efalizumab, natalizumab, tocilizumab, eculizumab, golimumab, canakinumab, ustekinumab, or belimumab. In certain embodiments, the additional therapeutic agent is a leucocyte depleting agent. In certain embodiments, the additional therapeutic agent is a B-cell depleting agent. In certain embodiments, the B-cell depleting agent is an antibody, e.g., an antibody that specifically binds to CD10, CD19, CD20, CD21, CD22, CD23, CD24, CD37, CD53, CD70, CD72, CD74, CD75, CD77, CD79a, CD79b, CD80, CD81, CD82, CD83, CD84, CD85, or CD86.

In another aspect, the instant disclosure provides a nucleic acid molecule encoding an FcRn-antagonist disclosed herein. In another aspect, the instant disclosure provides an expression vector comprising a nucleic acid molecule encoding an FcRn-antagonist disclosed herein. In another aspect, the instant disclosure provides a host cell comprising an expression vector or nucleic acid encoding an FcRn-antagonist disclosed herein. In another aspect, the instant disclosure provides a method of producing an FcRn-antagonist, the method comprising culturing a host cell disclosed herein under conditions such that an FcRn-antagonist is expressed.

BRIEF DESCRIPTION OF THE DRAWINGS

FIG. 5 depicts the results of ELISA assays comparing the affinity of Fc-Abdeg,Fc-Abdeg-POT and Fc-Abdeg-S239D/I332E for human CD16a.

DETAILED DESCRIPTION

Figure 1:
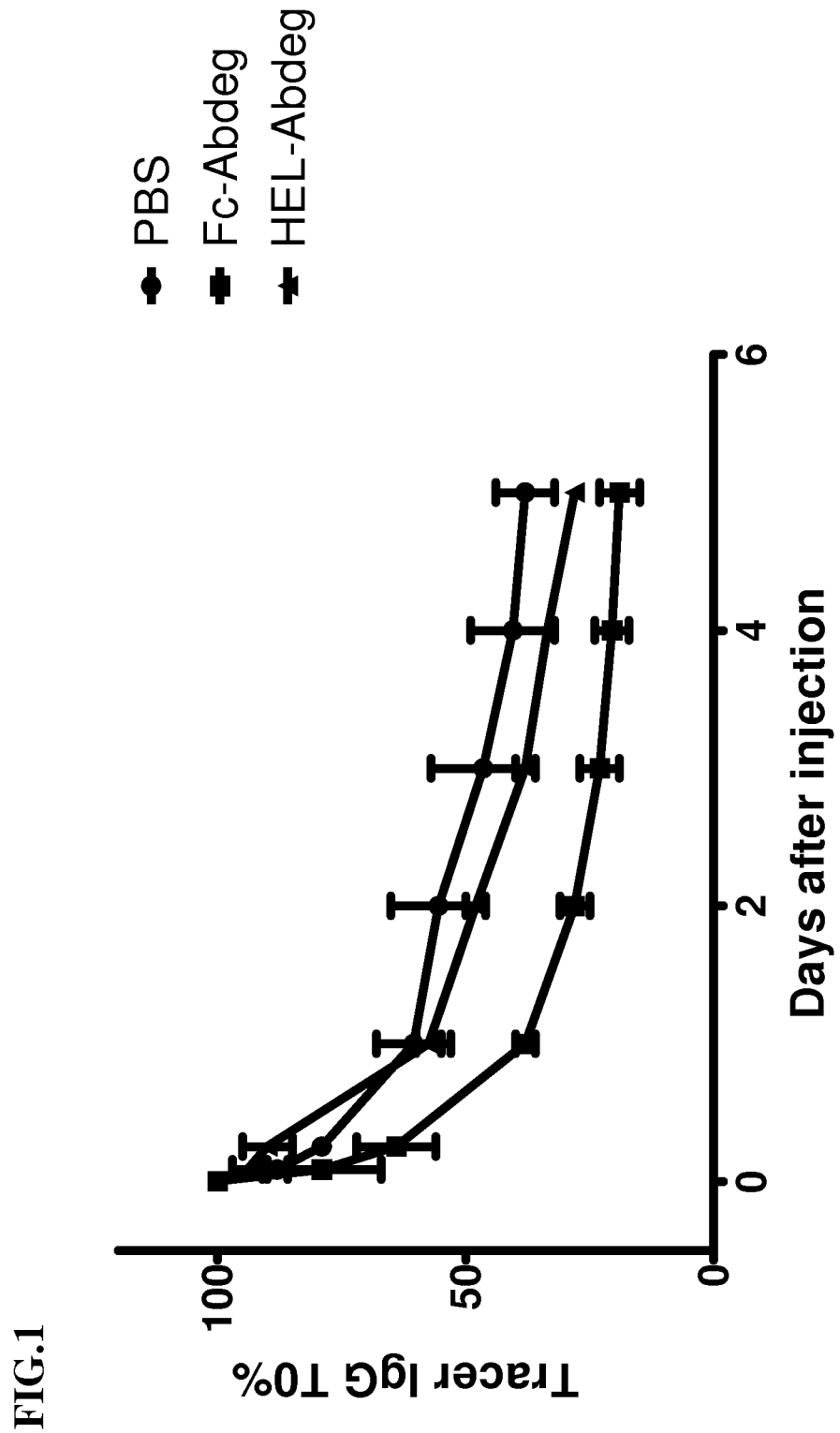
FIG. 1 depicts the results of experiments to determine the effect of Fc-Abdeg and HEL-Abdeg on the serum levels of a tracer antibody (FR70-hIgG1) in cynomolgous monkey.

The present disclosure provides novel FcRn antagonist compositions. These compositions generally comprise a variant Fc region, or FcRn-binding fragment thereof, that binds specifically to FcRn with increased affinity and reduced pH dependence relative to the native Fc region. The invention is based, in part, on the surprising finding that an isolated variant Fc region (e.g., a variant Fc region comprising the amino acids Y, T, E, K, F, and Y at EU positions 252, 254, 256, 433, 434, and 436 respectively) is a more efficacious FcRn antagonist in vivo than a full-length antibody comprising that variant Fc region. The FcRn antagonist compositions of the present disclosure are particularly useful for reducing the serum levels of Fc-containing agents (e.g., antibodies and immunoadhesins). Accordingly, the instant disclosure also provides methods of treating antibody-mediated disorder (e.g. autoimmune diseases) using the FcRn antagonist compositions disclosed herein. Also provided are nucleic acids encoding the FcRn antagonist compositions, recombinant expression vectors and host cells for making the FcRn antagonist compositions, and pharmaceutical compositions comprising the FcRn antagonist compositions.

I. Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

In order that the present invention may be more readily understood, certain terms are first defined.

As used herein the term "FcRn antagonist" refers to any agent comprising an Fc region (e.g., a variant Fc region disclosed herein) that binds specifically to FcRn through the Fc region and inhibits the binding of immunoglobulin to FcRn, with the proviso that the agent is not a full length IgG antibody.

As used herein, the term "Fc region" refers to the portion of a native immunoglobulin formed by the Fc domains of its two heavy chains. A native Fc region is homodimeric.

As used herein, the term "variant Fc region" refers to an Fc region with one or more alteration relative to a native Fc region. Alteration can include amino acid substitutions, additions and/or deletions, linkage of additional moieties, and/or alteration the native glycans. The term encompasses heterodimeric Fc regions where each of the constituent Fc domains is different. Examples of such heterodimeric Fc regions include, without limitation, Fc regions made using the "knobs and holes" technology as described in, for example, U.S. Pat. No. 8,216,805, which is incorporated by reference herein in its entirety. The term also encompasses single chain Fc regions where the constituent Fc domains are linked together by a linker moiety, as described in, for example, US20090252729A1 and US20110081345A1, which are each incorporated by reference herein in their entirety.

As used herein, the term "Fc domain" refers to the portion of a single immunoglobulin heavy chain beginning in the hinge region just upstream of the papain cleavage site and ending at the C-terminus of the antibody. Accordingly, a complete Fc domain comprises at least a portion of a hinge (e.g., upper, middle, and/or lower hinge region) domain, a CH2 domain, and a CH3 domain.

As used herein the term "FcRn binding fragment" refers to a portion of an Fc region that is sufficient to confer FcRn binding.

As used herein, the term "EU position" refers to the amino acid position in the EU numbering convention for the Fc region described in Edelman, G. M. et al., Proc. Natl. Acad. USA, 63, 78-85 (1969) and Kabat et al, in "Sequences of Proteins of Immunological Interest", U.S. Dept. Health and Human Services, 5th edition, 1991.

As used herein, the term "CH1 domain" refers to the first (most amino terminal) constant region domain of an immunoglobulin heavy chain that extends from about EU positions 118-215. The CH1 domain is adjacent to the VH domain and amino terminal to the hinge region of an immunoglobulin heavy chain molecule, and does not form a part of the Fc region of an immunoglobulin heavy chain.

As used herein, the term "hinge region" refers to the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 161: 4083 (1998)). The FcRn antagonists of the instant disclosure can include all or a portion of a hinge region.

As used herein, the term "CH2 domain" refers to the portion of a heavy chain immunoglobulin molecule that extends from about EU positions 231-340.

As used herein, the term "CH3 domain" includes the portion of a heavy chain immunoglobulin molecule that extends approximately 110 residues from N-terminus of the CH2 domain, e.g., from about position 341-446 (EU numbering system).

As used herein, the term "FcRn" refers to a neonatal Fc receptor. Exemplary FcRn molecules include human FcRn encoded by the FCGRT gene as set forth in RefSeq NM_004107.

As used herein, the term "CD16" refers to FcγRIII Fc receptors that are required for Antibody-Dependent Cell-mediated Cytotoxicity (ADCC). Exemplary CD16 molecules include human CD16a as set forth in RefSeq NM_000569.

As used herein, the term "free cysteine" refers to native or engineered cysteine amino acid residue that exists in a substantially reduced form in a mature FcRn antagonist.

As used herein, the term "antibody" refers to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL). The VH and VL regions can be further subdivided into regions of hypervariability, termed complementarity determining regions (CDRs), interspersed with regions that are more conserved, termed framework regions (FR).

As used herein the term "N-linked glycan" refers to the N-linked glycan attached to the nitrogen (N) in the side chain of asparagine in the sequon (i.e., Asn-X-Ser or Asn-X-Thr sequence, where X is any amino acid except proline) present in the CH2 domain of an Fc region. Such N-Glycans are fully described in, for example, Drickamer K, Taylor M E (2006). Introduction to Glycobiology, 2nd ed., which is incorporated herein by reference in its entirety.

As used herein the term "afucosylated" refers to an N-linked glycan which lacks a core fucose molecule as described in U.S. Pat. No. 8,067,232, the contents of which is incorporated by reference herein in its entirety.

As used herein the term "bisecting GlcNac" refers to an N-linked glycan having an N-acetylglucosamine (GlcNAc) molecule linked to a core mannose molecule, as described in U.S. Pat. No. 8,021,856, the contents of which is incorporated by reference herein in its entirety.

As used herein, the term "antibody-mediated disorder" refers to any disease or disorder caused or exacerbated by the presence of an antibody in a subject.

As used herein, the term "Fc-containing agent" is any molecule that comprises an Fc region.

As used herein, the term "leucocyte depleting agent" refers to an agent that reduces the number of leucocytes in a subject upon administration.

As used herein, the term "B-cell depleting agent" refers to an agent that reduces the number of B-cells in a subject upon administration.

As used herein, the term "T-cell depleting agent" refers to an agent that reduces the number of T-cells in a subject upon administration.

As used herein, the term "autoimmune channelopathy" refers to a diseases caused by autoantibodies against an ion channel subunit or a molecule that regulates the channel.

As used herein, the term "treat," "treating," and "treatment" refer to therapeutic or preventative measures described herein. The methods of "treatment" employ administration to a subject, an antibody or antigen binding fragment thereof of the present invention, for example, a subject having an IL-6-associated disease or disorder (e.g. inflammation and cancer) or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment. As used herein, the term "subject" includes any human or non-human animal.

As used herein, the term "immunoadhesin" refers to an antibody-like molecule, which comprises a functional domain of a binding protein (e.g., a receptor, ligand, or cell-adhesion molecule) with an Fc region.

II. FcRn Antagonists

In one aspect, the invention provides novel FcRn antagonist compositions. In general, these compositions comprise a variant Fc region, or FcRn-binding fragment thereof, that binds specifically to FcRn with increased affinity and reduced pH dependence relative to a native Fc region. These FcRn antagonists inhibit the binding of Fc-containing agents (e.g., antibodies and immunoadhesins) to FcRn in vivo, which results in an increased rate of degradation of the Fc-containing agents and, concomitantly, a reduced serum level of these agents.

The instant specification discloses, for the first time, that an isolated variant Fc region (e.g., a variant Fc region comprising the amino acids Y, T, E, K, F, and Y at EU positions 252, 254, 256, 433, 434, and 436 respectively) is a more efficacious FcRn antagonist in vivo than a full-length antibody comprising the same variant Fc region. Accordingly, in certain embodiments, the FcRn antagonist compositions are not full-length antibodies. In certain embodiments, the FcRn antagonist compositions do not comprise an antibody variable domain. In certain embodiments, the FcRn antagonist compositions do not comprise an antibody variable domain or a CH1 domain. However, in certain embodiments, the FcRn antagonist compositions may comprise a variant Fc region linked to one or more additional binding domains or moieties, including antibody variable domains.

Any Fc region can be altered to produce a variant Fc region for use in the FcRn antagonist compositions disclosed herein. In general, an Fc region, or FcRn-binding fragment thereof, is from a human immunoglobulin. It is understood, however, that the Fc region may be derived from an immunoglobulin of any other mammalian species, including for example, a Camelid species, a rodent (e.g. a mouse, rat, rabbit, guinea pig) or non-human primate (e.g. chimpanzee, macaque) species. Moreover, the Fc region or portion thereof may be derived from any immunoglobulin class, including IgM, IgG, IgD, IgA and IgE, and any immunoglobulin isotype, including IgG1, IgG2, IgG3 and IgG4. In certain embodiments, the Fc region is an IgG Fc region (e.g., a human IgG region). In certain embodiments, the Fc region is an IgG1 Fc region (e.g., a human IgG1 region). In certain embodiments, the Fc region is a chimeric Fc region comprising portions of several different Fc regions. Suitable examples of chimeric Fc regions are set forth in US20110243966A1, which is herein incorporated by reference in its entirety. A variety of Fc region gene sequences (e.g. human constant region gene sequences) are available in the form of publicly accessible deposits. It will be appreciated that the scope of this invention encompasses alleles, variants and mutations of Fc regions.

An Fc region can be further truncated or internally deleted to produce a minimal FcRn-binding fragment thereof. The ability of an Fc-region fragment to bind to FcRn can be determined using any art recognized binding assay e.g., ELISA.

To enhance the manufacturability of the FcRn antagonists disclosed herein, it is preferable that the constituent Fc regions do not do comprise any non-disulphide bonded cysteine residues. Accordingly, in certain embodiments the Fc regions do not comprise a free cysteine residue.

Any Fc variant, or FcRn-binding fragment thereof, that binds specifically to FcRn with increased affinity and reduced pH dependence relative to the native Fc region can be used in the FcRn antagonist compositions disclosed herein. In certain embodiments, the variant Fc region comprises amino acid alterations, substitutions, insertions and/or deletions that confer the desired characteristics. In certain embodiments, the variant Fc region or fragment comprises the amino acids Y, T, E, K, F, and Y at EU positions 252, 254, 256, 433, 434, and 436 respectively. Non-limiting examples of amino acid sequences that can be used in variant Fc regions are set forth in Table 1, herein. In certain embodiments, the amino acid sequence of the Fc domains of the variant Fc region comprises the amino acid sequence set forth in SEQ ID NO:1. In certain embodiments, the amino acid sequence of the Fc domains of the variant Fc region consists of the amino acid sequence set forth in SEQ ID NO:1, 2, or 3. In certain embodiments an FcRn-antagonist consists of a variant Fc region, wherein the amino acid sequence of the Fc domains of the variant Fc region consists of the amino acid sequence set forth in SEQ ID NO:1, 2, or 3.

TABLE 1

Amino acid sequences of non-limiting examples of variant Fc regions

| SEQ ID NO | Amino Acid Sequence |
| --- | --- |
| 1 | CPPCPAPELLGGPSVFLFPPKPKDTLYITREPEVTCVVVDVSHEDPEVKFNWYVD GVEVHNAKTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESNGQPENN YKTTPPVLDSDGSFFLYSKLTVDKSRWQQGNVFSCSVMHEALKFHYTQKSLSLSP G |
| 2 | DKTHTCPPCPAPELLGGPSVFLFPPKPKDTLYITREPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALKFHYTQKS LSLSPGK |
| 3 | DKTHTCPPCPAPELLGGPSVFLFPPKPKDTLYITREPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNG QPENNYKTTPPVLDSDGSFELYSKLTVDKSRWQQGNVESCSVMHEALKFHYTQKS LSLSPG |

Amino acids at EU positions 252, 254, 256, 433, and 434 are underlined

In certain embodiments, the variant Fc region has altered (e.g., increased or decreased) binding affinity for an additional Fc receptor. The variant Fc region can have altered (e.g., increased or decreased) binding affinity for one or more of Fcγ receptors e.g., FcγRI (CD64), FcγRIIA (CD32), FcγRIIB (CD32), FcγRIIIA (CD16a), and FcγRIIIB (CD16b). Any art recognized means of altering the affinity for an additional Fc receptor can be employed. In certain embodiments, the amino acid sequence of the variant Fc region is altered.

In certain embodiments, the variant Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217, the contents of which are incorporated by reference herein in their entirety).

In certain embodiments, the variant Fc region comprises at least one non-naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241R, 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264F, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217, the contents of which are incorporated by reference herein in their entirety).

Other known Fc variants that may be used in the FcRn antagonists disclosed herein include without limitations those disclosed in Ghetie et al., 1997, Nat. Biotech. 15:637-40; Duncan et al, 1988, Nature 332:563-564; Lund et al., 1991, J. Immunol., 147:2657-2662; Lund et al, 1992, Mol. Immunol., 29:53-59; Alegre et al, 1994, Transplantation 57:1537-1543; Hutchins et al., 1995, Proc Natl. Acad Sci USA, 92:11980-11984; Jefferis et al, 1995, Immunol Lett., 44:111-117; Lund et al., 1995, Faseb J., 9:115-119; Jefferis et al, 1996, Immunol Lett., 54:101-104; Lund et al, 1996, J. Immunol., 157:4963-4969; Armour et al., 1999, Eur a Immunol 29:2613-2624; Idusogie et al, 2000, J. Immunol., 164:4178-4184; Reddy et al, 2000, J. Immunol., 164:1.925-1933; Xu et al., 2000, Cell Immunol., 200:16-26; Idusogie et al, 2001, J. Immunol., 166:2571-2575; Shields et al., 2001, J Biol. Chem., 276:6591-6604; Jefferis et al, 2002, Immunol Lett., 82:57-65; Presta et al., 2002, Biochem Soc Trans., 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351, the contents of which are incorporated by reference herein in their entirety.

In certain embodiments, the variant Fc region is a heterodimer, where the constituent Fc domains are different from each other. Methods of producing Fc heterodimers are known in the art (see e.g., U.S. Pat. No. 8,216,805, which is incorporated by reference herein in its entirety). In certain embodiments, the variant Fc region is a single chain Fc region, where the constituent Fc domains are linked together by a linker moiety. Methods of producing single chain Fc regions are known in the art (see e.g., US20090252729A1 and US20110081345A1, which are each incorporated by reference herein in their entirety).

It is believed that pathogenic IgG antibodies observed in autoimmune diseases are either the pathogenic triggers for these diseases or contribute to disease progression and mediate disease through the inappropriate activation of cellular Fc receptors. Aggregated autoantibodies and/or autoantibodies complexed with self antigens (immune complexes) bind to activating Fc receptors, causing numerous autoimmune diseases (which occur in part because of immunologically mediated inflammation against self tissues) (see e.g., Clarkson et al., NEJM 314(9), 1236-1239 (2013)); US20040010124A1; US20040047862A1; and US2004/0265321A1, which are each incorporated by reference herein in their entirety). Accordingly, to treat antibody-mediated disorders (e.g. autoimmune diseases), it would be advantageous to both remove the deleterious autoantibodies and to block the interaction of the immune complexes of these antibodies with activating Fc receptors (e.g., Fcγ receptors, such as CD16a).

Accordingly, in certain embodiments, the variant Fc region of the FcRn antagonist exhibits increased binding to CD16a (e.g., human CD16a). This is particularly advantageous in that it allows the FcRn antagonist to additionally antagonize the immune complex-induced inflammatory response of autoantibodies being targeted for removal by FcRn inhibition. Any art recognized means of increasing affinity for CD16a (e.g., human CD16a) can be employed. In certain embodiments, the FcRn-antagonist comprises a variant Fc-region comprising an N-linked glycan (e.g., at EU position 297). In this case it is possible to increase the binding affinity of the FcRn-antagonist for CD16a by altering the glycan structure. Alterations of the N-linked glycan of Fc regions are well known in the art. For example, afucosylated N-linked glycans or N-glycans having a bisecting GlcNac structure have been shown to exhibit increased affinity for CD16a. Accordingly, in certain embodiments, the N-linked glycan is afucosylated. Afucosylation can be achieved using any art recognized means. For example, an FcRn-antagonist can be expressed in cells lacking fucosyl transferase, such that fucose is not added to the N-linked glycan at EU position 297 of the variant Fc region (see e.g., U.S. Pat. No. 8,067,232, the contents of which is incorporated by reference herein in its entirety). In certain embodiments, the N-linked glycan has a bisecting GlcNac structure. The bisecting GlcNac structure can be achieved using any art recognized means. For example, an FcRn-antagonist can be expressed in cells expressing beta1-4-N-acetylglucosaminyltransferase III (GnTIII), such that bisecting GlcNac is added to the N-linked glycan at EU position 297 of the variant Fc region (see e.g., U.S. Pat. No. 8,021,856, the contents of which is incorporated by reference herein in its entirety). Additionally or alternatively, alterations of the N-linked glycan structure can also be achieved by enzymatic means in vitro.

In certain embodiments, the instant disclosure provides FcRn-antagonist compositions wherein a portion of the FcRn-antagonist molecules contained therein comprise altered glycan structures. In certain embodiments, the FcRn-antagonist composition comprises a plurality of FcRn-antagonist molecules disclosed herein, wherein at least 50% (optionally, at least 60, 70, 80, 90, 95, or 99%) of the molecules comprise an Fc region or FcRn-binding fragment thereof having an afucosylated N-linked glycan. In certain embodiments, the FcRn-antagonist composition comprising a plurality of FcRn-antagonist molecules disclosed herein, wherein at least 50% (optionally, at least 60, 70, 80, 90, 95, or 99%) of the molecules comprise an Fc region or FcRn-binding fragment thereof comprising an N-linked glycan having a bisecting GlcNac.

In certain embodiments, the variant Fc region does not comprise an N-linked glycan. This can be achieved using any art recognized methods. For example, the Fc variant can be expressed in a cell that is incapable of N-linked glycosylation. Additionally or alternatively, the amino acid sequence of the Fc variant can be altered to prevent or inhibit N-linked glycosylation (e.g., by mutation of the NXT sequon). Alternatively, the Fc variant can be synthesized in an acellular system (e.g., chemically synthesized).

In certain embodiments, FcRn-antagonist molecules may be modified, e.g., by the covalent attachment of a molecule (e.g., a binding or imaging moiety) to the FcRn-antagonist such that covalent attachment does not prevent the FcRn-antagonist from specifically binding to FcRn. For example, but not by way of limitation, the FcRn-antagonist may be modified by glycosylation, acetylation, pegylation, phosphorylation, amidation, derivatization by known protecting blocking groups, proteolytic cleavage, linkage to a cellular ligand or other protein, etc.

In certain embodiments, the FcRn antagonist comprises a variant Fc region linked to a half-life extender. As used herein, the term "half-life extender" refers to any molecule that, when linked to an FcRn antagonist disclosed herein, increases the half-life of an FcRn antagonist. Any half-life extender may be linked (either covalently or non-covalently) to the FcRn antagonist. In certain embodiments, the half-life extender is polyethylene glycol or human serum albumin. In certain embodiments, the FcRn antagonist is linked to a binding molecule that specifically binds to a half-life extender present in a subject, such as a blood-carried molecule or cell, such as serum albumin (e.g., human serum albumin), IgG, erythrocytes, etc.

The FcRn antagonists disclosed herein have excellent manufacturability. For example, as shown in Example 5 herein, they can be expressed at high levels in mammalian cells (e.g., at 6 g/L in CHO cells in a 10 L stirred tank bioreactor). Moreover, after Protein A purification, the resultant purified FcRn antagonist composition has a very high percentage of FcRn antagonist monomers, and contains an extremely low level of FcRn antagonist protein aggregates and degradation products. Accordingly, in certain embodiments, the instant disclosure provides an FcRn antagonist composition comprising a plurality of FcRn antagonist molecules as disclosed herein, wherein greater than 95% the of the FcRn antagonist molecules in the composition are monomers (e.g., greater than 95, 96, 97, 98, 99, 99.1, 99.2, 99.3, 99.4, 99.5, 99.6, 99.7, 99.8, 99.9%). In certain embodiments, the instant disclosure provides an FcRn antagonist composition comprising a plurality of FcRn antagonist molecules disclosed herein, wherein less than 5% the of the FcRn antagonist molecules in the composition are present in aggregates, (e.g., less than 5, 4, 3, 2, 1, 0.9, 0.8, 0.7, 0.6, 0.5, 0.4, 0.3, 0.2, 0.1%). In certain embodiments, the instant disclosure provides an FcRn antagonist composition comprising a plurality of FcRn antagonist molecules disclosed herein, wherein the composition is substantially free of FcRn antagonist molecule degradation products.

III. Uses of FcRn Antagonists

The FcRn antagonist compositions of the present disclosure are particularly useful for reducing the serum levels of Fc-containing agents (e.g., antibodies and immunoadhesins). Accordingly, in one aspect the instant disclosure provides a method of inhibiting FcRn function in a subject, the method generally comprising administering to the subject an effective amount of an FcRn antagonist composition (e.g., a pharmaceutical composition) disclosed herein.

The reduction of serum levels of Fc-containing agents (e.g., antibodies and immunoadhesins) is particularly applicable to the treatment of antibody-mediated disorders (e.g. autoimmune diseases). Accordingly, in one aspect the instant disclosure provides methods of treating antibody-mediated disorders (e.g. autoimmune diseases) using the FcRn antagonist compositions disclosed herein.

Any antibody-mediated disorder can be treated using the FcRn antagonist compositions disclosed herein. In certain embodiments, the antibody-mediated disorder is one that is amenable to treatment by IVIG. In certain embodiments, the antibody-mediated disorder is an autoimmune disease. Non-limiting autoimmune diseases include allogenic islet graft rejection, alopecia areata, ankylosing spondylitis, antiphospholipid syndrome, autoimmune Addison's disease, Alzheimer's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac sprue-dermatitis, chronic fatigue immune disfunction syndrome, chronic inflammatory demyelinating polyneuropathy (CIDP), Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenic purpura (ITP), IgA neuropathy, IgM polyneuropathies, immune mediated thrombocytopenia, juvenile arthritis, Kawasaki's disease, lichen planus, lupus erythematosus, Meniere's disease, mixed connective tissue disease, multiple sclerosis, type 1 diabetes mellitus, Multifocal motor neuropathy (MMN), myasthenia gravis, paraneoplastic bullous pemphigoid, pemphigus vulgaris, pemphigus *foliaceus*, pernicious anemia, polyarteritis *nodosa*, polychrondritis, polyglandular syndromes, polymyalgia rheumatica, polymyositis and dermatomyositis, primary agammaglobinulinemia, primary biliary cirrhosis, psoriasis, psoriatic arthritis, Reynaud's phenomenon, Reiter's syndrome, rheumatoid arthritis, sarcoidosis, scleroderma, Sjögren's syndrome, solid organ transplant rejection, stiff-man syndrome, systemic lupus erythematosus, Takayasu arteritis, toxic epidermal necrolysis (TEN), Stevens Johnson syndrome (SJS), temporal arteritis/giant cell arteritis, thrombotic thrombocytopenia purpura, ulcerative colitis, uveitis, dermatitis herpetiformis vasculitis, anti-neutrophil cytoplasmic antibody-associated vasculitides, vitiligo, and Wegner's granulomatosis.

In certain embodiments, the autoimmune disease is an autoimmune channelopathy. Non-limiting channelopathies include neuromyelitis optica, Lambert-Eaton myasthenic syndrome, myasthenia gravis, anti-N-Methyl-D-aspartate (NMDA) receptor encephalitis, anti-α-Amino-3-hydroxy-5-methyl-4-isoxazolepropionic acid (AMPA) receptor encephalitis, Morvan syndrome, and Glycine receptor antibody-associated disorder.

The FcRn antagonist compositions of the instant disclosure are particularly suited to treating antibody-mediated disorders characterized by an over production of serum immunoglobulin. Accordingly, in certain embodiments, the FcRn antagonist compositions are used to treat hypergammaglobulinemia.

The FcRn antagonist compositions can also be used in combination with one or more additional therapeutic agents. In certain embodiments, the additional therapeutic agent is an anti-inflammatory agent. Any inflammatory agent can be used in combination with the compositions disclosed herein. In certain embodiments, the therapeutic agent is rituximab, daclizumab, basiliximab, muronomab-CD3, infliximab, adalimumab, omalizumab, efalizumab, natalizumab, tocilizumab, eculizumab, golimumab, canakinumab, ustekinumab, or belimumab. In certain embodiments, the additional therapeutic agent is leucocyte depleting agent (e.g., B-cell or T-cell depleting agent). Any leucocyte depleting agent can be used in combination with the FcRn antagonist compositions disclosed herein. In certain embodiments, the leucocyte depleting agent is a B-cell depleting agent. In certain embodiments, the leucocyte depleting agent is an antibody against a cell surface marker. Suitable cell surface markers include, without limitation, CD10, CD19, CD20, CD21, CD22, CD23, CD24, CD37, CD53, CD70, CD72, CD74, CD75, CD77, CD79a, CD79b, CD80, CD81, CD82, CD83, CD84, CD85, or CD86. The FcRn antagonist and the additional therapeutic agent(s) can be administered to the subject simultaneously or sequentially, via the same or different route(s) of administration.

The FcRn antagonist compositions of the instant disclosure are also well suited to rapidly reducing the serum levels of an Fc-containing agent in subject. Such rapid clearance is advantageous in cases where the Fc-containing agent is toxic (e.g., an antibody-drug conjugate or an agent that is immunogenic) because it reduces the exposure of the subject to the drug. Rapid clearance is also advantageous in cases where the Fc-containing agent is an imaging agent that requires a low serum level of the agent to facilitate imaging. Accordingly, in certain embodiments, the FcRn antagonist compositions are used to reduce the serum levels of an Fc-containing agent in subject that has been administered the Fc-containing agent. The serum levels of any Fc-containing agent (e.g., therapeutic or diagnostic agent) can be reduced using the FcRn antagonist compositions disclosed herein. Non limiting examples of Fc-containing agents include imaging agents (e.g., labeled antibodies), antibody drug conjugates, or immunogenic agents (e.g., non-human antibodies or immunoadhesins). The FcRn antagonist can be administered simultaneously with the Fc-containing agent or sequentially (e.g., before or after the Fc-containing agent).

Furthermore, in diseases or conditions requiring administration of a therapeutic agent, the subject will often develop antibodies (e.g., anti-drug antibodies) against the therapeutic agent, which, in turn, prevent the therapeutic agent from being available for its intended therapeutic purpose or cause an adverse reaction in the subject. Accordingly, the FcRn antagonist compositions disclosed herein can also be used to remove antibodies (e.g., anti-drug antibodies) against the therapeutic agent that develop in a subject.

The FcRn antagonist compositions disclosed herein can also be used in combination with the therapeutic protein to enhance the benefit of the therapeutic protein by reducing the levels of IgG; wherein, IgG antibodies are responsible for the decreased bioavailability of a therapeutic protein. In certain embodiments the instant disclosure provides a method of treating a disorder resulting from an immune response to a clotting factor comprising administering to a subject a therapeutically effective amount of an FcRn antagonist compositions disclosed herein. Suitable clotting factors include, without limitation, fibrinogen, prothrombin, factor V, factor VII, factor VIII, factor IX, factor X, factor XI, factor XII, factor XIII, or von Willebrand's factor. This method may be used to regulate or treat, or prevent an immune response to a clotting factor in a patient suffering, e.g., from hemophilia A or hemophilia B. In certain embodiments, the method may be used to regulate or treat an immune response to, e.g., therapeutic erythropoietin in a patient suffering from pure red cell aplasia (PRCA).

FcRn is responsible for transporting maternal antibodies across the placenta to the fetus in a pregnant woman. Accordingly, if a pregnant female is administered an Fc-containing agent (e.g., a therapeutic antibody), the agent may come in contact with the fetus as a result of the FcRn-mediated transport across the placenta. To avoid any potential deleterious effect of the Fc-containing agent on fetal development, it would be advantageous to block FcRn function. Accordingly, the instant disclosure provides a method of preventing placental transfer of an Fc-containing agent (e.g., a therapeutic antibody) to the fetus in a pregnant woman, the method comprising administering to the woman an FcRn antagonist compositions disclosed herein, either simultaneously or sequentially (prior or post) with the Fc-containing agent.

The FcRn antagonist compositions disclosed herein can also be used to treat inflammatory disorders including, but not limited to, asthma, ulcerative colitis and inflammatory bowel syndrome allergy, including allergic rhinitis/sinusitis, skin allergies (urticaria/hives, angioedema, atopic dermatitis), food allergies, drug allergies, insect allergies, mastocytosis, arthritis, including osteoarthritis, rheumatoid arthritis, and spondyloarthropathies.

Successful implementation of gene therapy for the treatment of a disease or condition may be hampered by the development of antibodies specific to the therapeutic protein encoded by the transgene as well as possibly to the vector used to deliver the transgene. Accordingly, the FcRn antagonist compositions disclosed herein can be administered in combination with gene therapy to enhance the benefit of the encoded therapeutic protein by reducing the levels of IgG. These methods are particularly useful in situations where IgG antibodies are responsible for the decreased bioavailability of a gene therapy vector or the encoded therapeutic protein. The gene therapy vector may be, e.g., a viral vector such as adenovirus and adeno-associated virus. Diseases that can be treated using gene therapy include, but are not limited to, cystic fibrosis, hemophilia, PRCA, muscular dystrophy, or lysosomal storage diseases, such as, e.g., Gaucher's disease and Fabry's disease.

One skilled in the art would be able, by routine experimentation, to determine what an effective, non-toxic amount of FcRn antagonist composition would be for the purpose of treating an antibody-mediated disorder. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.1 to 10,000 mg/kg body weight per day e.g., about 1 to 1000, about 10-500, or about 50-250 or mg/kg body weight per day (e.g., about 70 mg/kg body weight per day.

IV. Pharmaceutical Compositions

In another aspect, the instant disclosure provides pharmaceutical compositions comprising an FcRn antagonist or FcRn antagonist composition disclosed herein and a pharmaceutically acceptable carrier or excipient. Examples of suitable pharmaceutical carriers are described in Remington's Pharmaceutical Sciences by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

The pharmaceutical composition can be formulated for parenteral administration (e.g., intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

FcRn antagonists may be linked to chelators such as those described in U.S. Pat. No. 5,326,856. The peptide-chelator complex may then be radiolabeled to provide an imaging agent for diagnosis or treatment of diseases or conditions involving the regulation of IgG levels.

V. Production of FcRn Antagonists

In one aspect, the invention provides polynucleotides, vectors and host cells encoding the FcRn antagonists disclosed herein. Methods of making an FcRn antagonists comprising expressing these polynucleotides are also provided.

Polynucleotides encoding the FcRn antagonists disclosed herein are typically inserted in an expression vector for introduction into host cells that may be used to produce the desired quantity of the claimed FcRn antagonists. Accordingly, in certain aspects, the invention provides expression vectors comprising polynucleotides disclosed herein and host cells comprising these vectors and polynucleotides.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed for the purposes of this invention. For example, one class of vector utilizes DNA elements, which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers that allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

More generally, once a vector or DNA sequence encoding an FcRn antagonist has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the FcRn antagonist, and assayed for FcRn antagonist expression. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of FcRn antagonist unless it is clearly specified otherwise. In other words, recovery of FcRn antagonist from the "cells" may mean either from spun down whole cells, or from the cell culture containing both the medium and the suspended cells.

In one embodiment, the host cell line used for FcRn antagonist expression is of mammalian origin; those skilled in the art can determine particular host cell lines, which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the FcRn antagonist expressed therefrom (e.g., PER.C6.® (Crucell) or FUT8-knock-out CHO cell lines (Potelligent™ Cells) (Biowa, Princeton, N.J.)). In one embodiment NSO cells may be used. CHO cells are particularly preferred. Host cell lines are typically available from commercial services, the American Tissue Culture Collection or from published literature.

In vitro production allows scale-up to give large amounts of the desired FcRn antagonist. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

Genes encoding the FcRn antagonists of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the FcRn antagonists can become part of inclusion bodies. The FcRn antagonists must be isolated, purified and then assembled into functional molecules. In addition to prokaryotes, eukaryotic microbes may also be used. *Saccharomyces cerevisiae*, or common baker's yeast, is the most commonly used among eukaryotic microorganisms although a number of other strains are commonly available.

In addition to cell-based expression systems, the FcRn antagonists can also be produced using acellular or chemically synthetic methods. In certain embodiments, the FcRn antagonists are produced by in vitro chemical synthesis.

IV. Exemplification

The present invention is further illustrated by the following examples, which should not be construed as further limiting. The contents of Sequence Listing, figures and all references, patents, and published patent applications cited throughout this application are expressly incorporated herein by reference.

Example 1: Effect of Fc-Abdeg on Serum IgG Levels in Cynomolgus Monkeys

Figure 2:
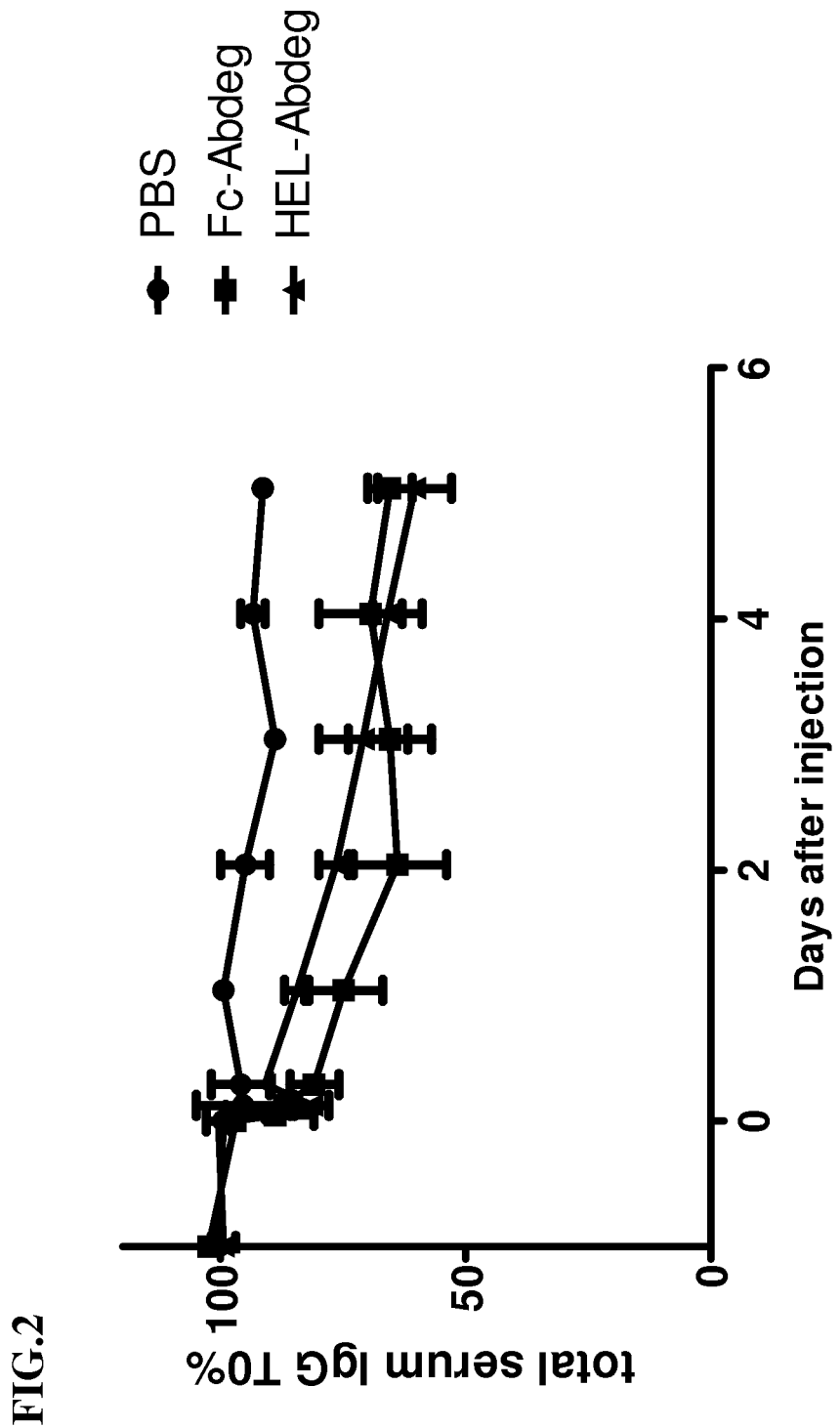
FIG. 2 depicts the results of experiments to determine the effect of Fc-Abdeg and HEL-Abdeg on total IgG serum levels in cynomolgous monkey.

The effect of a human anti-lysozyme IgG (HEL-Abdeg) and a human IgG Fc region (Fc-Abdeg), comprising the amino acids Y, T, E, K, F, and Y at EU positions 252, 254, 256, 433, 434, and 436, respectively (Fc-Abdeg; SEQ ID NO:2), on serum IgG levels of a tracer antibody was determined in cynomolgus monkeys. Specifically, cynomolgus monkeys were administered 1 mg/kg of an anti-murine CD70 hIgG1 tracer antibody (FR70-hIgG1; Oshima et al., Int Immunol 10(4): 517-26 (1998)) by i.v. bolus injection. Animals were infused 5 minutes later with either 7 mg/kg Fc-Abdeg, 20 mg/kg HEL-Abdeg, or PBS (2 monkeys per group). Infusion was performed within 1 hour and animals were administered a volume of 10 ml/kg. Blood samples (3×150 µl) were taken at 5 min prior to dosing ("pre-dose") and 5 min, 2 h, 6 h, 24 h, 48 h, 72 h, 96 h and 120 h after completion of the infusion. Tracer levels were determined by performing a mCD70-binding ELISA and data were plotted relative to tracer levels at end of dosing (FIG. 1). Total cynomolgus IgG levels were also determined (FIG. 2). The results of these experiments show that Fc-Abdeg reduced tracer antibody more efficiently than equimolar amounts of HEL-Abdeg.

Figure 3:
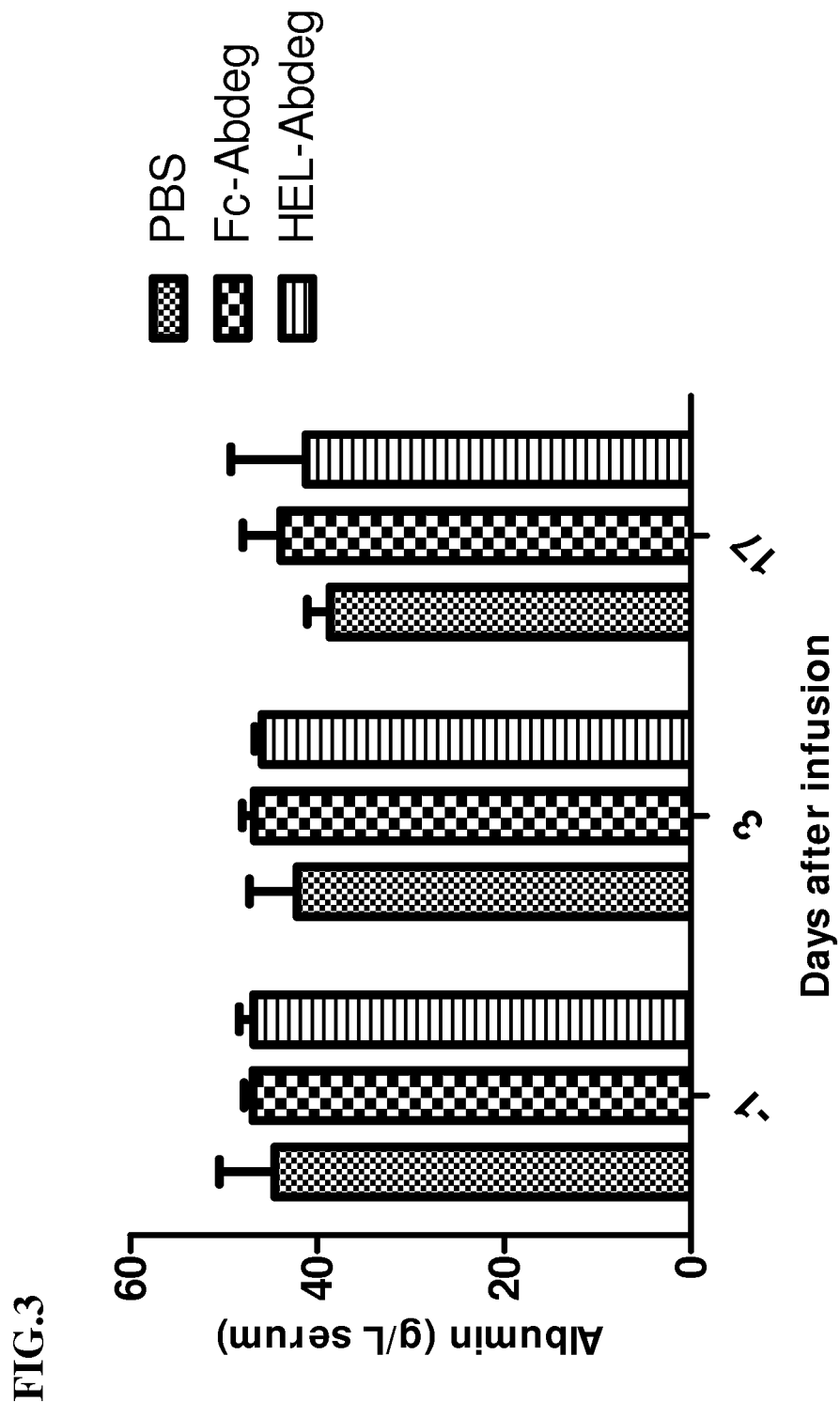
FIG. 3 depicts the results of experiments the effect of Fc-Abdeg and HEL-Abdeg on albumin levels in cynomolgous monkey.

In addition to its key role in the IgG salvage pathway, FcRn is also involved in albumin homeostasis (Chaudhury et al., J Exp Med. 197(3):315-22 (2003). FcRn interacts with IgG-Fc and albumin at distinct sites and binding can happen concurrently (Andersen et al., Nat Commun. 3:610 (2012)). Conceptually, blockage of IgG recycling using Abdeg-modified molecules should not interfere with albumin-FcRn interaction. This hypothesis was confirmed in a mouse in vivo study, where the authors showed no influence of an Abdeg-equipped hIgG1 molecule on albumin levels (Patel et al., J Immunol 187(2): 1015-22 (2011)). In the experiment described above, albumin levels were also determined at day −3, day 3 and day 17 after the completion of the infusion. Analogous to the mouse study, no significant changes in albumin levels were observed after Fc-Abdeg or HEL-Abdeg treatment (see FIG. 3).

Figure 4:
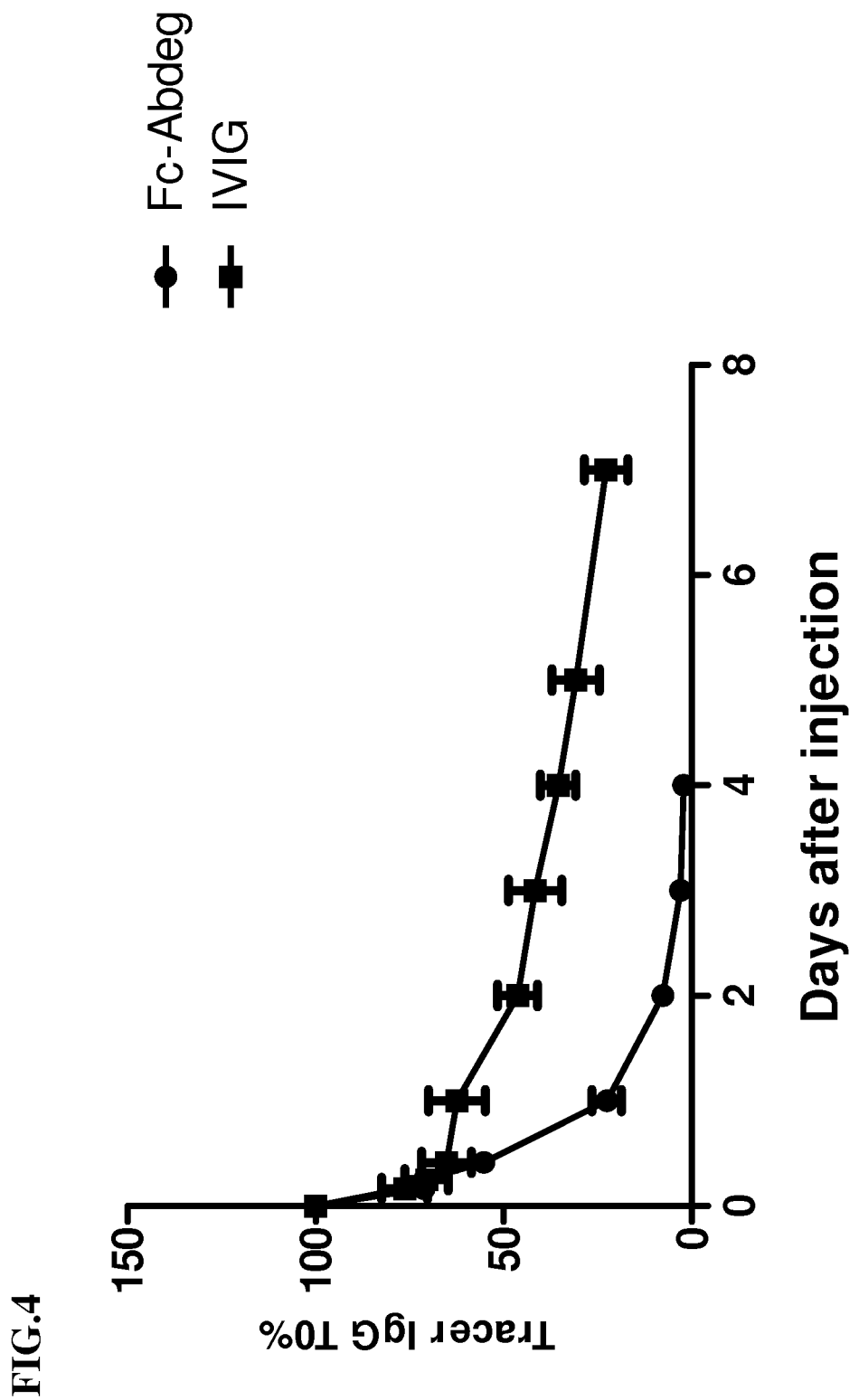
FIG. 4 depicts the results of experiments to determine the effect of Fc-Abdeg and IVIG on the serum levels of a tracer antibody (FR70-hIgG1) in cynomolgous monkey.

In a subsequent experiment, the antibody-depleting potency of Fc-Abdeg was compared to IVIG. Specifically, cynomolgus monkeys were administered with 1 mg/kg tracer antibody (FR70-hIgG1) 2 days prior to dosing with 70 mg/kg Fc-Abdeg or 2 g/kg IVIG (2 monkeys per group). Infusion of Fc-Abdeg and IVIG was performed within 4 hours and animals were administered a volume of 20 ml/kg. Blood (3×150 µl) samples were taken 5 min prior to dosing ("pre-dose"), and 5 min, 2 h, 6 h, 24 h, 48 h, 72 h, 96 h, 120 h, and 168 h after completion of the infusion. Tracer levels were determined by mCD70-binding ELISA and plotted relative to pre-dose levels (FIG. 4). In comparison with IVIG treatment at clinical dose (2 g/kg), 70 mg/kg Fc-Abdeg showed significantly enhanced kinetics of tracer clearance and was also able to clear more efficiently (>95% tracer clearance in 4 days for Abdeg versus ~75% in 7 days for IVIG).

Example 2: Effect of Afucosylation on Fc-Abdeg Affinity for Human CD16a and Murine CD16-2

The binding affinity of Fc-Abdeg for hCD16a was determined and compared to the afucosylated form (Fc-Abdeg-POT). In the same experiment an Fc-Abdeg variant showing improved affinity for all FcγRs was included ("Fc-Abdeg-S239D/I332E). Specifically, a Maxisorp plate was coated with 100 ng/well of Neutravidin Biotin-binding Protein (ThermoScientific, 31000) and incubated overnight at 4° C. The following day, the plate was blocked with PBS+1% casein for 2 hours at room temperature. Subsequently, 100 µl/well of a 250 ng/ml solution (dilution in PBS+0.1% casein) of biotinylated hCD16a (Sino Biological Inc., 10389-H27H1-B) was added to the plate and incubated for 1 hour at room temperature prior to applying a concentration gradient of Fc-Abdeg or Fc-Abdeg-POT molecules (1 µM-0.005 nM) for a further hour. Binding to hCD16a was detected using an HRP-conjugated polyclonal goat anti-human Fc antibody (Jackson ImmunoResearch, 109-035-008) (incubation 1 hour at RT, dilution 1/50,000 in PBS+

Figure 5:
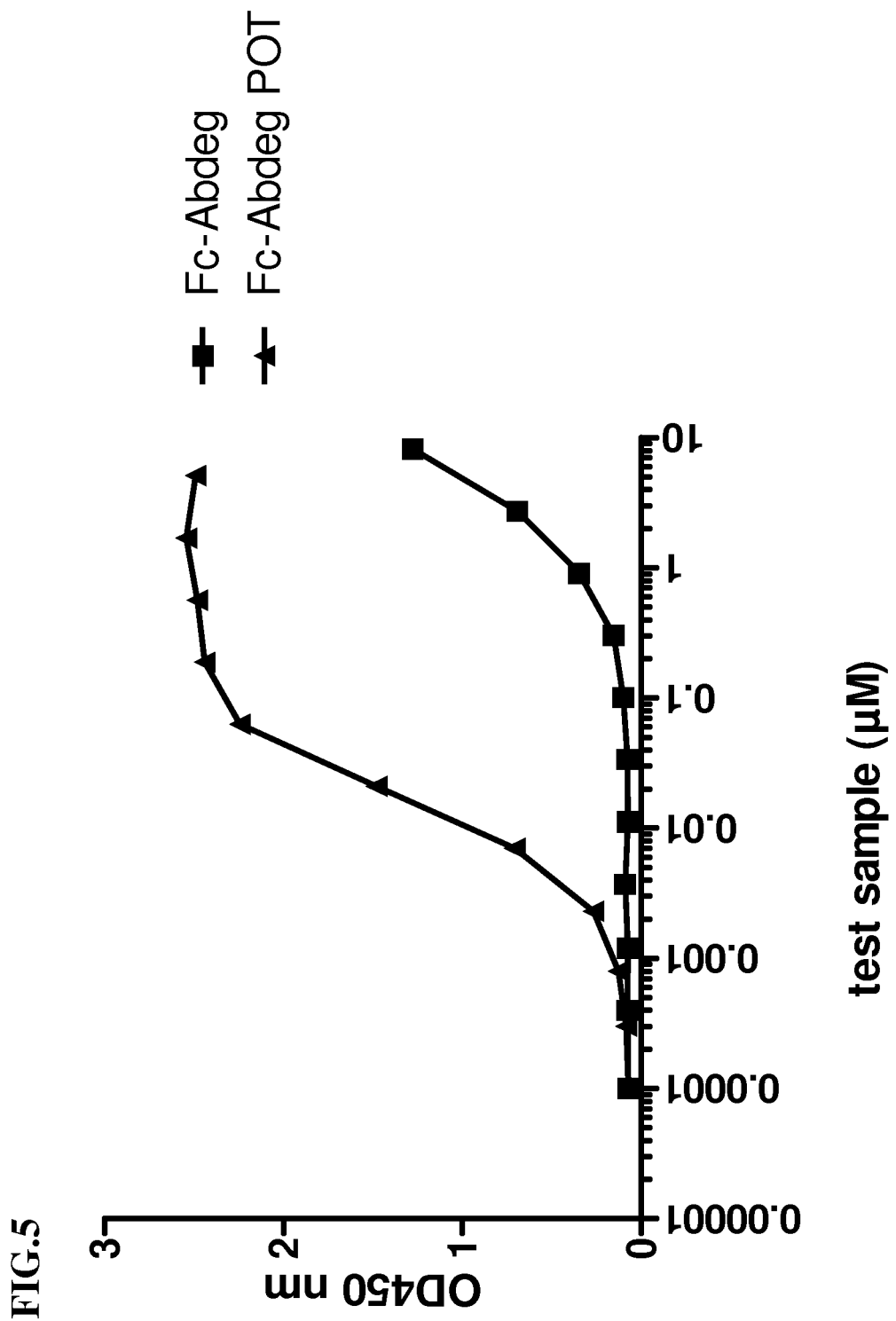

0.1% casein), followed by addition of 1000 room temperature-equilibrated TMB (SDT-reagents #s TMB). Plates were incubated for 10 minutes prior to addition of 100 µl 0.5N $H_2SO_4$ and OD450 nm measurement. EC50 values were determined using GraphPad Prism software. The results of these experiments, set forth in FIG. 5, show that defucosylation of the Fc-Abdeg molecule results in a >30-fold increase in affinity for hCD16a ($EC_{50}$=13 nM for the Fc-Abdeg-POT vs. $EC_{50}$>0.4 µM for the fucosylated Fc-Abdeg). As expected, binding affinity of the Fc-Abdeg-S239D/I332E variant for hCD16a was increased compared to wild-type Fc-Abdeg ($EC_{50}$=6 nM).

Figure 6:
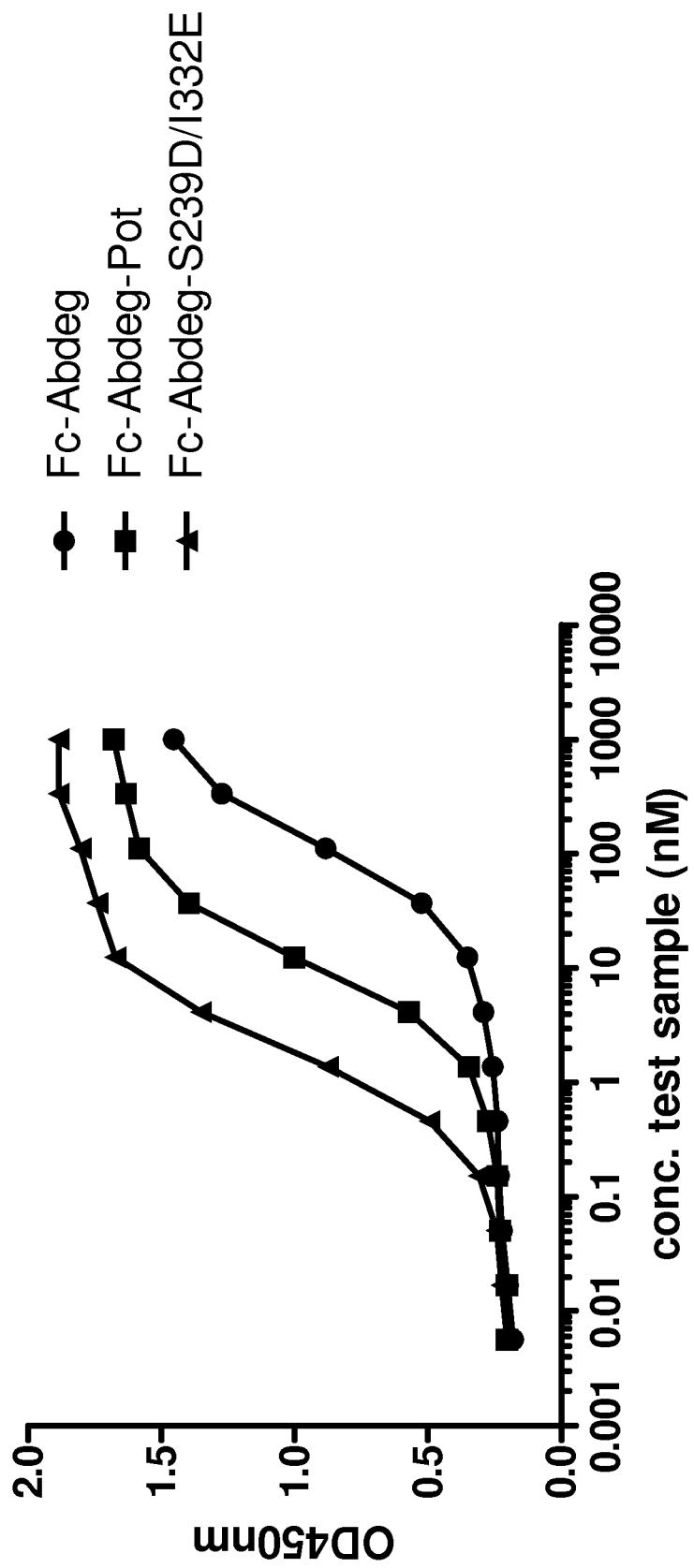
FIG. 6 depicts the results of ELISA assays comparing the affinity of Fc-Abdeg,Fc-Abdeg-POT and Fc-Abdeg-S239D/I332E for murine CD16-2.

Using a similar experimental procedure as described above, the binding affinity for murine CD16-2 (Sino Biological Inc., 50036-M27H-B) was determined. The results of these experiments, set forth in FIG. 6, again show an increased affinity of the afucosylated variant compared to the wild-type Fc-Abdeg ($EC_{50}$=11 nM vs. $EC_{50}$>100 nM). The fold increase in affinity for mCD16-2 of the Fc-Abdeg-POT variant over the wild-type Fc-Abdeg is lower compared to that observed for binding to human CD16a. This effect was not observed for the Fc-Abdeg-S239D/I332E variant ($EC_{50}$=2 nM), which has a similar fold increase in affinity over wild type Fc-Abdeg for both the human and murine CD16 ($EC_{50}$=2 nM).

Autoantibodies complexed with self antigens bind to activating FcγRs and thereby trigger the autoimmune diseases, which occur in part because of immunologically mediated inflammation against self tissue. The ability of Fc-Abdeg to antagonize the interaction of autoimmune antibodies and FcγRIII receptors on NK cells was evaluated in two ADCC-based assays.

Figure 7:
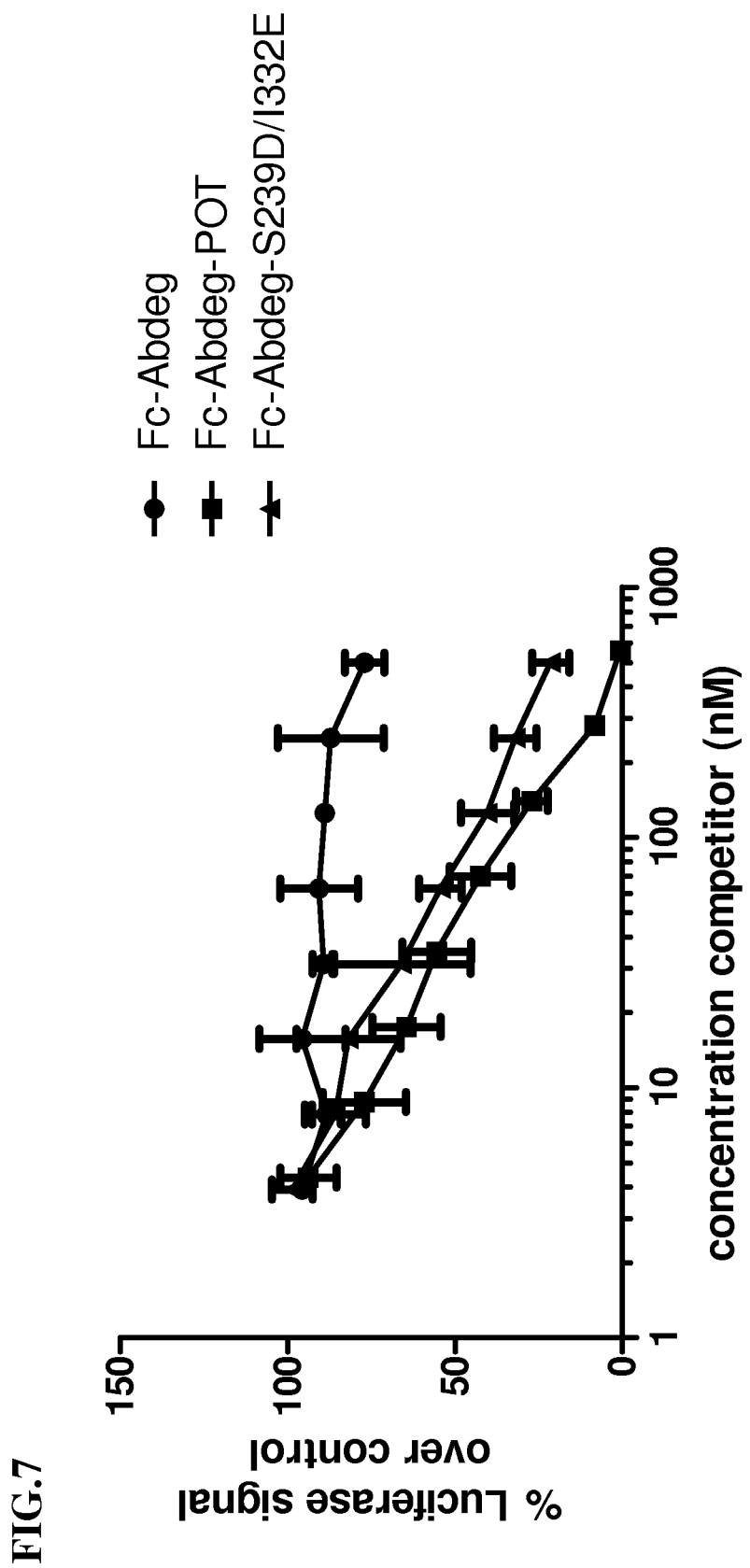
FIG. 7 depicts the results of experiments to determine the effect of Fc-Abdeg, Abdeg-POT and Fc-AbdegS239D/I332E on anti-CD20-induced ADCC-signal using the Promega's Raji-based ADCC reporter bioassay.

Initially, an ADCC reporter bioassay (Promega, G7016) was used to analyze the competitive hCD16a binding potency of Fc-Abdeg, Fc-Abdeg-POT and Fc-Abdeg-S239D/I332E. Specifically, 10,000 CD20-expressing Raji cells (target cells) were incubated with 60,000 Jurkat cells expressing hCD16a (effector cells) in presence of 100 ng/ml anti-CD20 antibody and increasing concentration of competitor. Cells were incubated for 6 hours at 37° C. prior to measuring the bioluminescence signal, which is a measure of ADCC-activity. The luciferase signal was plotted relative to the signal obtained by 100 ng/ml anti-CD20 in the absence of competitor (see FIG. 7). These experiments demonstrate that both Fc-Abdeg-POT and Fc-Abdeg-S239D/I332E efficiently block the anti-CD20-induced ADCC signal, whilst incubation with wild-type Fc-Abdeg does not lead to competitive binding for hCD16a expressed on Jurkat cells.

Figure 8:
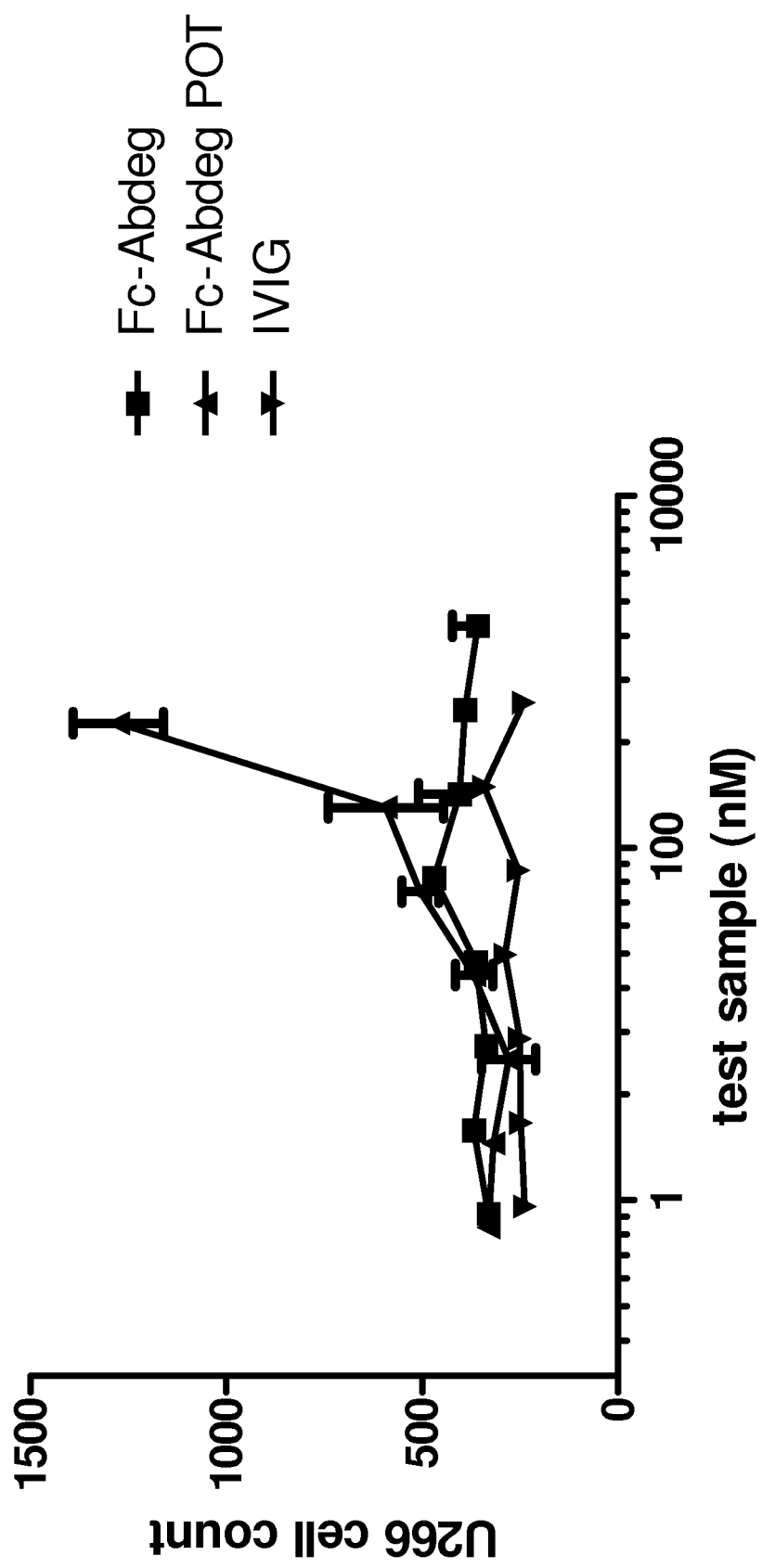
FIG. 8 depicts the results of experiments to determine the effect of Fc-Abdeg and Abdeg-POT on anti-CD70-induced lysis of CD70+U266 cells in vitro.

In a next ADCC assay, inhibition of the lytic activity of an anti-hCD70 antibody (27B3-hIgG1) by Fc-Abdeg and Fc-Abdeg-POT was tested as a measure of competitive hCD16 binding. Specifically, about 50,000 hCD70-expressing U266 cells were spiked into about 300,000 freshly purified PBMCs from a healthy donor in the presence of 50 ng/ml of the anti-hCD70 antibody and a concentration-gradient of Fc-Abdeg, Fc-Abdeg-POT and IVIG. The U266 cells were incubated for two days, and subsequent cell lysis was analyzed by FACS using a marker specific for the U266 cells (CD28). The results of these experiments, set forth in FIG. 8, show that the anti-CD70 antibody efficiently lyses U266 cells and that this depletion could be attenuated in a dose-dependent fashion by addition of Fc-Abdeg-POT but not by wild-type Fc-Abdeg nor IVIG. These data demonstrate that Fc-Abdeg POT has enhanced competitive CD16a binding properties relative to wild-type Fc-Abdeg and IVIG.

Example 3: Murine Acute ITP Model

Figure 9:
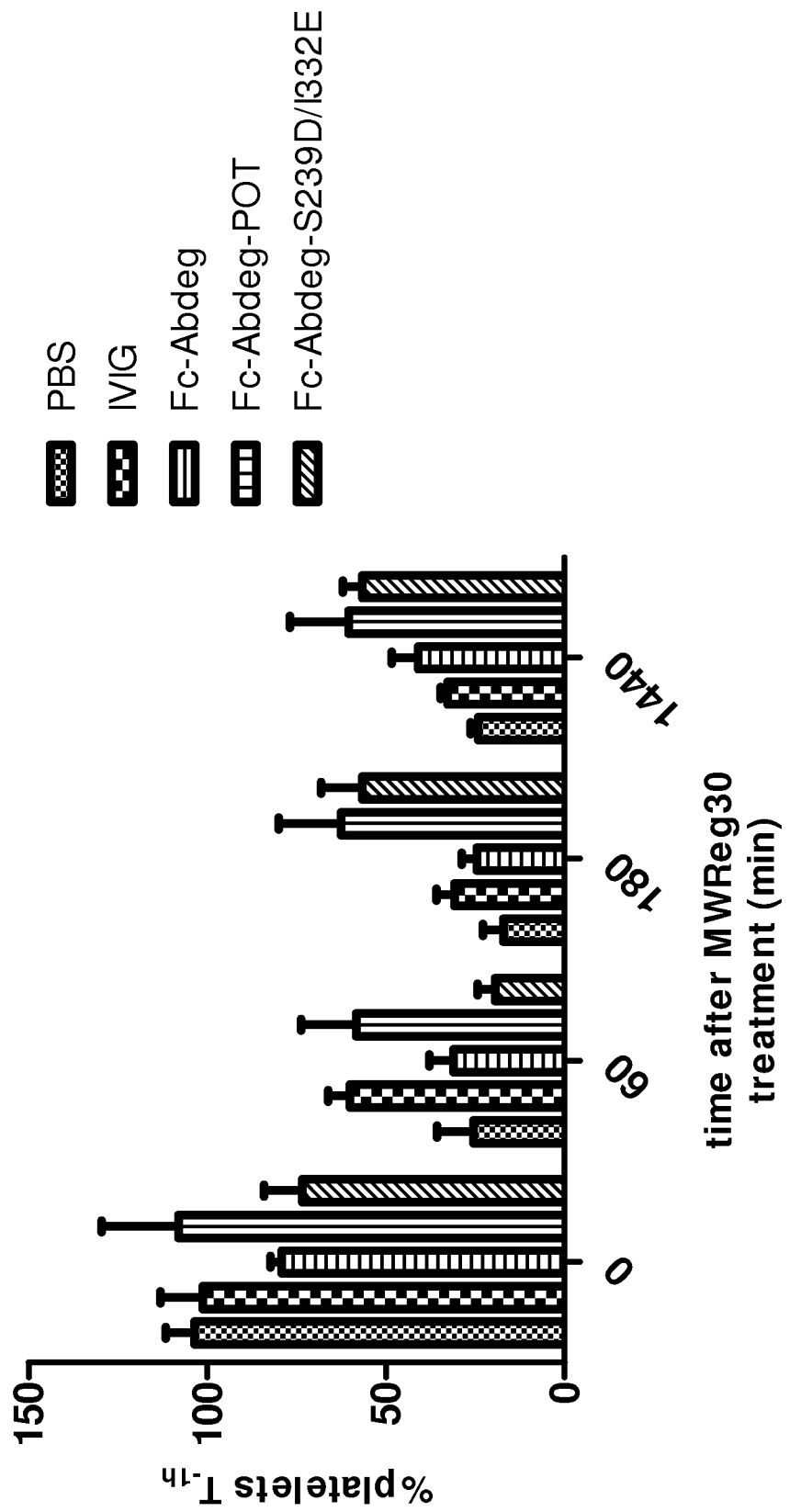
FIG. 9 depicts the results of experiments to determine the effect of Fc-Abdeg, Fc-Abdeg-POT, Fc-Abdeg-S239D/I332E and IVIG on platelet levels in an acute murine model for immune thrombocytopenia.

The therapeutic potency of Fc-Abdeg, Fc-Abdeg-POT, Fc-Abdeg-S239D/I332E molecules was tested in a mouse model of acute immune thrombocytopenia. Specifically, C57BL/6 mice were treated with IVIG (20 mg/animal), Fc-Abdeg (1 mg/animal), Fc-Abdeg-POT (1 mg/animal), Fc-Abdeg-S239D/I332E (1 mg/animal) or saline via the intraperitoneal infusion (5 animals/group). Prior to treatment, a blood sample was withdrawn for a baseline measurement of platelet counts. One hour later, mice were treated with 5 µg/animal of the anti-mouse platelet antibody MWReg30 (Nieswandt et al., Blood 94:684-93 (1999)). Platelet counts were monitored over 24 hours. Platelet counts were normalized relative to the initial counts for each mouse and platelets numbers were determined using flow cytometry via anti-CD61 staining. The results of these experiments, set forth in FIG. 9, demonstrate that pretreatment with Fc-Abdeg reduces MWReg30-induced thrombocytopenia with a similar potency compared to a 7-fold higher molar dose of IVIG, and further, that blockade of FcγRs by Fc-Abdeg POT and Fc-Abdeg-S239D/I332E had a synergistic beneficial effect in this model, as seen by the improved platelet counts at the 180 and 1440 minutes time points.

Example 4: Manufacturability Fc-Abdeg

Fc-Abdeg (comprising Fc domains having SEQ ID NO:2) was produced in CHO cells (Evitria, Switzerland) by transient transfection. Following transfection, high titers of Fc-Abdeg were detected in the supernatants (between 200 and 400 mg/ml). A similar favorable production profile was seen when Fc-Abdeg was expressed from an expression construct stably integrated into the CHO GS-XCEED cell line (Lonza, Great-Britain). On average, stable transfectants yielded 3 g/L and several clones were identified which produced up to 6 g/L Fc-Abdeg in a 10 L stirred tank bioreactor.

Figure 10:
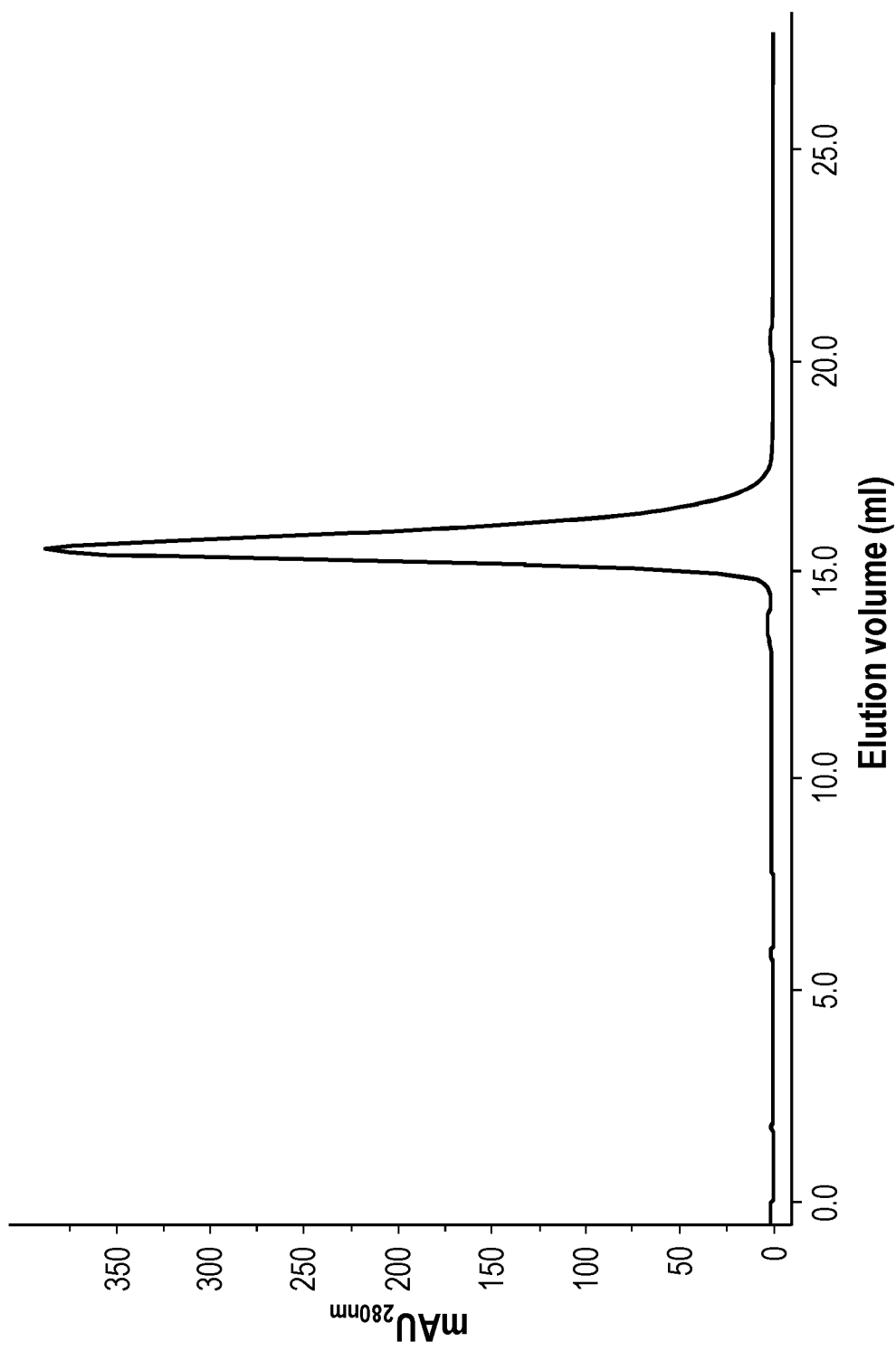
FIG. 10 depicts the result of an exemplary gelfiltration purification of Fc-Abdeg.

The manufacturability of the Fc-Abdeg was further investigated by analysis of aggregates and degradation products following protein A-purification of the aforementioned Fc-Abdeg production runs. Specifically, 137 µg of Fc-Abdeg was loaded on a Superdex 200 10/300 GL gelfiltration column (GE Healthcare) coupled to an AktaPurifier chromatography system. Results of this experiment, set forth in FIG. 10, showed that only a very small percentage of Fc-Abdeg aggregates was observed (~0.5%), whilst no Fc-Abdeg degradation products were detected. Additionally, applying various stress conditions (freeze-thaw, rotational or temperature stress) to the protein A-purified Fc-Abdeg did not lead to any apparent change in physicochemical and functional properties. Taken together, these data demonstrate the excellent manufacturability of the Fc-Abdeg.

We claim:

1. A method of treating myasthenia gravis in a subject, the method comprising administering to the subject an effective amount of an isolated FcRn antagonist consisting of a variant Fc region, wherein said variant Fc region consists of two Fc domains which form a homodimer, wherein the amino acid sequence of each of the Fc domains consists of SEQ ID NO: 2.

2. The method of claim 1, wherein the Fc domains of the variant Fc region comprise an N-linked glycan having a bisecting GlcNac at EU position 297 of the Fc domains.

3. The method of claim 1, wherein the FcRn antagonist is administered to the subject simultaneously or sequentially with a CD20 antibody.

4. The method of claim 1, wherein the FcRn antagonist is administered to the subject simultaneously or sequentially with rituximab.

5. The method of claim 1, wherein the FcRn antagonist is administered to the subject simultaneously or sequentially with eculizumab.

6. A method of treating myasthenia gravis in a subject, the method comprising administering to the subject an effective amount of an isolated FcRn antagonist consisting of a variant Fc region, wherein said variant Fc region consists of two Fc domains which form a homodimer, wherein the amino acid sequence of each of the Fc domains consists of SEQ ID NO: 3.

7. The method of claim 6, wherein the Fc domains of the variant Fc region comprise an N-linked glycan having a bisecting GlcNac at EU position 297 of the Fc domains.

8. The method of claim 6, wherein the FcRn antagonist is administered to the subject simultaneously or sequentially with a CD20 antibody.

9. The method of claim 6, wherein the FcRn antagonist is administered to the subject simultaneously or sequentially with rituximab.

10. The method of claim 6, wherein the FcRn antagonist is administered to the subject simultaneously or sequentially with eculizumab.

* * * * *

UNITED STATES PATENT AND TRADEMARK OFFICE
CERTIFICATE OF CORRECTION

PATENT NO. : 11,505,585 B2
APPLICATION NO. : 15/821104
DATED : November 22, 2022
INVENTOR(S) : Peter Ulrichts et al.

It is certified that error appears in the above-identified patent and that said Letters Patent is hereby corrected as shown below:

On the Title Page

At Item (72), Inventors:
"Peter Ulrichts, Destelbergeb (BE)" should read --Peter Ulrichts, Destelbergen (BE)--;
"Christophe Blanchetot, Destellbergen (BE)" should read --Christophe Blanchetot, Destelbergen (BE)--.

Signed and Sealed this
Eleventh Day of April, 2023

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Tyr Ile Thr Arg Glu Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu Lys
        195                 200                 205

Phe His Tyr Thr Gln Lys Ser Leu Ser Leu Ser Pro Gly
    210                 215                 220

<210> SEQ ID NO 2
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr

```
            65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu Lys Phe His Tyr Thr Gln Lys Ser Leu Ser Leu Ser
    210                 215                 220
Pro Gly Lys
225

<210> SEQ ID NO 3
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Tyr
            20                  25                  30
Ile Thr Arg Glu Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
        195                 200                 205
His Glu Ala Leu Lys Phe His Tyr Thr Gln Lys Ser Leu Ser Leu Ser
        210                 215                 220
Pro Gly
225
```